US008725418B2

(12) United States Patent
Aerts et al.

(10) Patent No.: US 8,725,418 B2
(45) Date of Patent: May 13, 2014

(54) DATA MINING OF SNP DATABASES FOR THE SELECTION OF INTRAGENIC SNPS

(75) Inventors: Jan Aerts, Wageningen (NL); Yves Wetzels, Hasselt (BE); Nadine Cohen, Warren, NJ (US); Jeroen Aerssens, Wilsele (BE)

(73) Assignee: Janssen Pharmaceutica, N.V., Beerse (BE)

( * ) Notice: Subject to any disclaimer, the term of this patent is extended or adjusted under 35 U.S.C. 154(b) by 974 days.

(21) Appl. No.: 10/325,981

(22) Filed: Dec. 23, 2002

(65) Prior Publication Data

US 2003/0190649 A1 Oct. 9, 2003

Related U.S. Application Data

(60) Provisional application No. 60/366,574, filed on Mar. 25, 2002.

(51) Int. Cl.
*G06F 19/00* (2011.01)
*G06F 19/10* (2011.01)

(52) U.S. Cl.
USPC .............................. 702/19; 702/20

(58) Field of Classification Search
USPC .......................................... 707/20
See application file for complete search history.

(56) References Cited

U.S. PATENT DOCUMENTS

| 5,324,631 | A | 6/1994 | Helentjaris et al. | |
|---|---|---|---|---|
| 5,645,995 | A | 7/1997 | Kieback | |
| 6,297,018 | B1 | 10/2001 | French et al. | |
| 6,322,980 | B1 | 11/2001 | Singh | |
| 6,691,109 | B2 * | 2/2004 | Bjornson et al. | 707/4 |
| 6,775,622 | B1 * | 8/2004 | Holloway | 702/20 |
| 6,898,531 | B2 * | 5/2005 | Sheehan et al. | 702/19 |
| 6,931,401 | B2 * | 8/2005 | Gibson et al. | 707/6 |
| 6,969,589 | B2 * | 11/2005 | Patil et al. | 435/6 |
| 2003/0023384 | A1 * | 1/2003 | Siani-Rose et al. | 702/19 |
| 2003/0068625 | A1 * | 4/2003 | Sheehan et al. | 435/6 |

FOREIGN PATENT DOCUMENTS

| WO | WO 00/18960 | 4/2000 |
|---|---|---|
| WO | WO 00/50869 | 8/2000 |

OTHER PUBLICATIONS

Riva A; Kohane IS. Journal of the American Medical Informatics Association. pp. 558-562, 2001.*
Cox et al. "Data Mining: Efficiency of using sequence databases for polymorphism discovery." Human Mutation, vol. 17, pp. 141-150, 2001.*
Powell et al. Hypervariable microsatellites provide a general source of polymorphic DNA markers for the chloroplast genome. Current Biology, 1995, vol. 5, pp. 1023-1029.*
Baens et al. Isolation and regional assignments of human chromosome 12p cDNAs. Genomics. vol. 29, 1995, pp. 44-52.*
Scott et al. Refining the DFN87-DFNB11 deafness locus using intragenic polymorphisms in a novel gene, TMEM2. Gene, 2000, vol. 246, pp. 265-274.*
Aerts et al., Human Mutation Suppl. Mat. Online, S1-S13 (2002).
J. Aerts et al. 20 20 Human Mutation 162-73 (2002).
Deutsch, S., et al., "A cSNP map and database for human chromosome 21," *Genome Res.*, 2001, 300-307.
Douabin-Gicquel, V., et al. "Identification of 96 single nucleotide polymorphisms in eight genes involved in iron metabolism: efficiency of bioinformatics extraction compared with a systematic sequencing approach," *Hum. Genet*, 2001, 109, 393-401.
Escary, J.-L., et al., "A first high-density map of 981 biallelic markers on human chromosome 14," *Genomics*, 2000, 70, 153-164.
Gu, Z., et al., "Single nucleotide polymorphism hunting in cyberspace," *Human Mutation*, 1998, 12; 221-225.
Sherry, S.T., et al., "dbSNP—database for single nucleotide polymorphisms and other classes of minor genetic variation," *Genome Res.*, 1999, 9, 677-679.
Alizadeh et al., "Distinct Types of Diffuse Large B-Cell Lymphoma Identified by Gene Expression Profiling," *Nature*, 2000; 403:503-511.
Altschul et al., "Gapped BLAST and PSI-BLAST: A New Generation of Protein Database Search Programs," *Nucleic Acids Res.*, 1997; 25(17):3389-3402.
Brookes et al., "HGBASE: A Database of SNPs and Other Variations in and Around Human Genes," *Nucl. Acids. Res.*, 2000; 28(1):356-360.
Brookes et al., "The Essence of SNPs," *Gene*, 1999; 234:177-186.
Cargill et al., "Characterization of Single-Nucleotide Polymorphisms in Coding Regions of Human Genes," *Nat. Genet.*, 1999; 22:231-238.
Cauchi et al., "Polymorphisms of Human Aryl Hydrocarbon Receptor (AhR) Gene in a French Population: Relationship with CYP1A1 Inducibility and Lung Cancer," *Carcinogenesis*, 2001; 22(11):1819-1824.
Chapman et al., "Linkage Disequilibrium Mapping: The Role of Population History, Size, and Structure," *Adv. Genet.*, 2001; 42:413-437.
Collins et al., "A DNA Polymorphism Discovery Resource for Research on Human Genetic Variation," *Genome Res.*, 1998; 8:1229-1231.
Crow et al., "Spontaneous Mutation as a Risk Factor," *Exp. Clin. Immunogenet.*, 1995; 12:121-128.
Drysdale et al., "Complex Promoter and Coding Region $\beta_2$-Adrenergic Receptor Haplotypes Alter Receptor Expression and predict In Vivo Responsiveness," *PNAS*, 2000; 97(19):10483-10488.
Gray et al., "Single Nucleotide Polymorphisms as Tools in Human Genetics," *Hum. Mol. Genet.*, 2000; 9(16):2403-2408.
Harding et al., "Archaic African and Asian Lineages in the Genetic Ancestry of Modern Humans," *Am. J. Human Genet.*, 1997; 60:772-789.
Johnson et al., "Haplotype Tagging for the Identification of Common Disease Genes," *Nat. Genet.*, 2001; 29:233-237.

(Continued)

*Primary Examiner* — Lori A Clow

(57) ABSTRACT

The present invention relates to data mining of SNP databases for the selection of intragenic SNPs. The present invention provides methodologies for annotating SNPs onto candidate genes based on appropriate sequence comparison software or algorithms such as a BLAST search of SNP databases. Additionally, the present invention provides methodologies useful in the selection of intragenic SNPs for genotyping in genetic studies.

61 Claims, 9 Drawing Sheets

(56) References Cited

OTHER PUBLICATIONS

Jurka et al., "Repbase Update: A Database and an Electronic Journal of Repetitive Elements," *TIG*, 2000; 16(9):418-420.

Kao et al., "The Role of Single Nucleotide Polymorphisms (SNPs) in Understanding Complex Disorders and Pharmacogenomics," *Ann. Acad. Med.* Singapore, 2000; 29:376-382.

Kondrashov et al., "Contamination of the Genome by Very Slightly Deleterious Mutations: Why Have We Not Died 100 Times Over," *J. Theor. Biol.*, 1995; 175:583-594.

Kwok et al., "Single Nucleotide Polymorphism Libraries: Why and How are we Building Them?" *Molecular Medicine Today*, 1999; 5:538-553.

Landegren et al., "Reading Bits of Genetic Information: Methods for Single-Nucleotide Polymorphism Analysis," *Genome Res.*, 1998; 8:769-776.

Lander et al., "Genetic Dissection of Complex Traits," *Science*, 1994; 265:2037-2048.

Raunio et al., "Polymorphisms of CYP2A6 and Its Practical Consequences," *Br. J. Clin. Pharmacol.*, 2001; 52:357-363.

Semple et al., "In Silico Identification of Transcripts and SNPs from a Region of 4p Linked with Bipolar Affective Disorder," *Bioinform Disc. Note*, 2000; 16(8):735-738.

Sherry et al., "dbSNP: The NCBI Database of Genetic Variation," *Nuci. Acids Res.*, 2001; 29(1):308-311.

Taillon-Miller et al., "Overlapping Genomic Sequences: A Treasure Trove of Single-Nucleotide Polymorphisms," *Genome Res.*, 1998; 8:748-754.

Van Der Put et al., "A Second Common Mutation in the Methylenetetrahydrofolate Reductase Gene: An Additional Risk Factor for Neural-Tube Defects?" *Am. J. Hum. Genet.*, 1998; 62:1044-1051.

Wang et al., "Large-Scale Identification, Mapping, and Genotyping of Single-Nucleotide Polymorphisms in the Human Genome," *Science*, 1998; 280:1077-1082.

Weisberg et al., "A Second Genetic Polymorphism in Methylenetetrahydrofolate Reductase (MTHFR) Associated with Decreased Enzyme Activity," *Mol. Genet. Metab.*, 1998; 64:169-172.

\* cited by examiner

| Gene | gDNA Working Draft location | mRNA Genbank Accession | OMIM Reference |
|---|---|---|---|
| ABCC2 | chr10:107186139-107255907 | NM_000392 | 601107 |
| AHR | chr7:16497123-16545269 | NM_001621 | 600253 |
| COMT | chr22:16868600-16896734 | NM_000754 | 116790 |
| CYP1A2 | chr15:71476562-71485318 | NM_000761 | 124060 |
| CYP2A6 | chr19:48317128-48325023 | NM_000762 | 122720 |
| CYP3A5 | chr7:100914305-100947094 | NM_000777 | 605325 |
| DIA1 | chr22:39531318-39560515 | NM_007326 | 250800 |
| FIGN | chr2:166707091-166710185 | NM_018086 | 605295 |
| FMO3 | chr1:192780592-192808359 | NM_006894 | 136132 |
| GSTM4 | chr1:120957118-120963406 | NM_000850 | 138333 |
| GSTP1 | chr11:71702072-71705901 | NM_000852 | 134660 |
| GSTT1 | chr22:21022190-21031280 | NM_000853 | 600436 |
| GSTT2 | chr22:20945658-20950432 | NM_000854 | 600437 |
| GSTZ1 | chr14:75768981-75780511 | NM_001513 | 603758 |
| MTHFR | chr1:12195380-12209036 | NM_005957 | 236250 |
| NAT2 | chr8:19782053-19784227 | NM_000015 | 243400 |
| NOS2 | chr17:29252826-29316071 | NM_000625 | 163730 |
| NOS3 | chr7:157454503-157476139 | NM_000603 | 163729 |
| NR3C1 | chr5:156499128-156534720 | NM_000176 | 138040 |
| RXRB | chr6:36178177-36185380 | NM_021976 | 180246 |
| RXRG | chr1:186726743-186771545 | NM_006917 | 180247 |
| STE | chr4:72685927-72705121 | NM_005420 | 600043 |
| UGT1A1 | chr2:240466042-240480062 | NM_000463 | 191740 |
| UGT2B15 | chr4:71768275-71793261 | NM_001076 | 600069 |

FIGURE 6

| Gene | total | total nonrepeat | promoter total | promoter nonrepeat | 5'UTR total | 5'UTR nonrepeat | CDS total | CDS nonrepeat | intron total | intron nonrepeat | 3'UTR total | 3'UTR nonrepeat |
|---|---|---|---|---|---|---|---|---|---|---|---|---|
| ABCC2 | 69,769 | 50,104 | 1,000 | 789 | 37 | 37 | 4,638 | 4,638 | 63,909 | 44,455 | 185 | 185 |
| AHR | 48,147 | 44,421 | 1,000 | 1,000 | 643 | 643 | 2,547 | 2,547 | 41,654 | 38,177 | 2,303 | 2,054 |
| COMT | 28,135 | 20,394 | 1,000 | 1,000 | 203 | 203 | 817 | 817 | 25,844 | 18,103 | 271 | 271 |
| CYP1A2 | 8,757 | 6,997 | 1,000 | 861 | 64 | 64 | 1,548 | 1,548 | 4,631 | 4,073 | 1,514 | 451 |
| CYP2A6 | 7,896 | 7,581 | 1,000 | 1,000 | 9 | 9 | 1,485 | 1,485 | 5,146 | 4,831 | 256 | 256 |
| CYP3A5 | 32,790 | 25,250 | 1,000 | 1,000 | 87 | 87 | 1,509 | 1,509 | 30,083 | 22,543 | 111 | 111 |
| DIA1 | 29,198 | 22,338 | 1,000 | 612 | 175 | 175 | 837 | 837 | 26,228 | 19,756 | 958 | 958 |
| FIGN | 3,095 | 3,095 | 1,000 | 1,000 | 162 | 162 | 1,920 | 1,920 | 0 | 0 | 13 | 13 |
| FMO3 | 27,768 | 21,451 | 1,000 | 1,000 | 93 | 93 | 1,599 | 1,599 | 24,855 | 18,538 | 221 | 221 |
| GSTM4 | 6,289 | 6,019 | 1,000 | 730 | 263 | 263 | 657 | 657 | 4,208 | 4,208 | 161 | 161 |
| GSTP1 | 3,830 | 3,398 | 1,000 | 568 | 29 | 29 | 633 | 633 | 2,099 | 2,099 | 69 | 69 |
| GSTT1 | 9,091 | 6,761 | 1,000 | 836 | 0 | 0 | 723 | 723 | 7,086 | 4,920 | 282 | 282 |
| GSTT2 | 4,775 | 4,198 | 1,000 | 1,000 | 64 | 64 | 735 | 735 | 2,674 | 2,097 | 302 | 302 |
| GSTZ1 | 11,531 | 10,680 | 1,000 | 1,000 | 103 | 103 | 651 | 651 | 9,376 | 8,525 | 401 | 401 |
| MTHFR | 13,657 | 11,683 | 1,000 | 1,000 | 12 | 12 | 1,971 | 1,971 | 10,469 | 8,495 | 205 | 205 |
| NAT2 | 2,175 | 2,175 | 1,000 | 1,000 | 107 | 107 | 873 | 873 | 0 | 0 | 195 | 195 |
| NOS2 | 63,246 | 44,247 | 1,000 | 822 | 194 | 194 | 3,462 | 3,462 | 58,391 | 39,570 | 199 | 199 |
| NOS3 | 21,637 | 19,777 | 1,000 | 1,000 | 20 | 20 | 3,612 | 3,612 | 16,947 | 15,087 | 58 | 58 |
| NR3C1 | 35,593 | 27,641 | 1,000 | 1,000 | 132 | 132 | 2,334 | 2,334 | 31,119 | 23,167 | 1,008 | 1,008 |
| RXRB | 7,204 | 6,961 | 1,000 | 1,000 | 179 | 179 | 1,602 | 1,602 | 4,193 | 3,950 | 230 | 230 |
| RXRG | 44,803 | 42,052 | 1,000 | 1,000 | 27 | 27 | 1,392 | 1,392 | 42,239 | 39,488 | 145 | 145 |
| STE | 19,195 | 17,228 | 1,000 | 1,000 | 106 | 106 | 885 | 885 | 17,150 | 15,183 | 54 | 54 |
| UGT1A1 | 14,021 | 11,703 | 1,000 | 773 | 15 | 15 | 1,602 | 1,602 | 10,670 | 8,579 | 734 | 734 |
| UGT2B15 | 24,987 | 15,613 | 1,000 | 637 | 21 | 21 | 1,593 | 1,593 | 21,908 | 13,037 | 465 | 325 |
| TOTAL | 537,589 | 431,767 | 24,000 | 21,628 | 2,745 | 2,745 | 39,625 | 39,625 | 460,879 | 358,881 | 10,340 | 8,888 |

FIGURE 7

| Gene | dbSNP | | | | | | HGBASE | | | | | | dbSNP and HGBASE merged | | | | | |
|---|---|---|---|---|---|---|---|---|---|---|---|---|---|---|---|---|---|---|
| | total | promoter | 5'UTR | CDS | intron | 3'UTR | total | promoter | 5'UTR | CDS | intron | 3'UTR | total | promoter | 5'UTR | CDS | intron | 3'UTR |
| ABCC2 | 10 | 0 | 1 | 1 | 8 | 0 | 34 | 0 | 1 | 1 | 32 | 0 | 41 | 0 | 1 | 1 | 39 | 0 |
| AHR | 5 | 0 | 0 | 1 | 3 | 1 | 3 | 0 | 0 | 0 | 1 | 2 | 8 | 0 | 0 | 1 | 4 | 3 |
| COMT | 44 | 1 | 1 | 8 | 31 | 3 | 32 | 0 | 1 | 9 | 20 | 2 | 45 | 1 | 1 | 9 | 31 | 3 |
| CYP1A2 | 1 | 0 | 0 | 0 | 1 | 0 | 0 | 0 | 0 | 0 | 0 | 0 | 1 | 0 | 0 | 0 | 1 | 0 |
| CYP2A6 | 9 | 0 | 0 | 5 | 2 | 2 | 1 | 0 | 0 | 1 | 0 | 0 | 9 | 0 | 0 | 5 | 2 | 2 |
| CYP3A5 | 4 | 0 | 0 | 0 | 3 | 1 | 2 | 0 | 0 | 0 | 1 | 1 | 5 | 0 | 0 | 0 | 4 | 1 |
| DIA1 | 28 | 1 | 0 | 1 | 23 | 3 | 33 | 0 | 0 | 1 | 29 | 3 | 35 | 1 | 0 | 1 | 30 | 3 |
| FIGN | 0 | 0 | 0 | 0 | 0 | 0 | 0 | 0 | 0 | 0 | 0 | 0 | 0 | 0 | 0 | 0 | 0 | 0 |
| FMO3 | 25 | 0 | 0 | 10 | 15 | 0 | 15 | 0 | 0 | 8 | 7 | 0 | 26 | 0 | 0 | 10 | 16 | 0 |
| GSTM4 | 15 | 2 | 0 | 3 | 9 | 1 | 12 | 2 | 0 | 3 | 9 | 0 | 18 | 2 | 0 | 4 | 11 | 1 |
| GSTP1 | 7 | 0 | 0 | 3 | 3 | 1 | 9 | 0 | 0 | 4 | 2 | 0 | 11 | 0 | 0 | 4 | 4 | 1 |
| GSTT1 | 13 | 0 | 0 | 4 | 8 | 1 | 14 | 0 | 0 | 6 | 7 | 1 | 17 | 0 | 0 | 6 | 10 | 1 |
| GSTT2 | 20 | 4 | 0 | 5 | 10 | 1 | 18 | 6 | 0 | 3 | 8 | 1 | 23 | 7 | 0 | 5 | 10 | 1 |
| GSTZ1 | 16 | 0 | 3 | 6 | 7 | 0 | 9 | 0 | 2 | 4 | 3 | 0 | 21 | 0 | 4 | 7 | 10 | 0 |
| MTHFR | 19 | 1 | 0 | 7 | 11 | 0 | 18 | 0 | 0 | 7 | 11 | 0 | 19 | 1 | 0 | 7 | 11 | 0 |
| NAT2 | 11 | 2 | 0 | 8 | 0 | 1 | 11 | 2 | 0 | 8 | 0 | 1 | 11 | 2 | 0 | 8 | 0 | 1 |
| NOS2 | 7 | 0 | 0 | 3 | 4 | 0 | 1 | 0 | 0 | 0 | 1 | 0 | 8 | 0 | 0 | 3 | 5 | 0 |
| NOS3 | 19 | 1 | 0 | 3 | 15 | 0 | 38 | 2 | 0 | 2 | 34 | 0 | 47 | 2 | 0 | 3 | 42 | 0 |
| NR3C1 | 18 | 0 | 0 | 6 | 10 | 2 | 8 | 0 | 0 | 5 | 1 | 2 | 18 | 0 | 0 | 6 | 10 | 2 |
| RXRB | 3 | 1 | 0 | 2 | 0 | 0 | 4 | 1 | 0 | 2 | 1 | 0 | 4 | 1 | 0 | 2 | 1 | 0 |
| RXRG | 67 | 1 | 0 | 2 | 64 | 0 | 55 | 1 | 0 | 2 | 52 | 0 | 67 | 1 | 0 | 2 | 64 | 0 |
| STE | 12 | 0 | 0 | 0 | 12 | 0 | 1 | 0 | 0 | 0 | 1 | 0 | 13 | 0 | 0 | 0 | 13 | 0 |
| UGT1A1 | 9 | 3 | 0 | 1 | 2 | 3 | 9 | 3 | 0 | 1 | 2 | 3 | 9 | 3 | 0 | 1 | 2 | 3 |
| UGT2B15 | 15 | 1 | 0 | 1 | 13 | 0 | 0 | 0 | 0 | 0 | 0 | 0 | 15 | 1 | 0 | 1 | 13 | 0 |
| TOTAL | 377 | 18 | 5 | 80 | 254 | 20 | 327 | 17 | 4 | 67 | 222 | 17 | 471 | 24 | 6 | 86 | 333 | 22 |

FIGURE 8

DATA MINING OF SNP DATABASES FOR THE SELECTION OF INTRAGENIC SNPS

CROSS-RELATED APPLICATION

This application is related to, and claims the benefit under 35 USC §119(e) of, U.S. Provisional Application No. 60/366,574, filed Mar. 25, 2002, which is incorporated expressly herein by reference.

FIELD OF THE INVENTION

The present invention relates to data mining of SNP databases for the selection of intragenic SNPs. The present invention provides methodologies for annotating SNPs onto candidate genes based on appropriate sequence comparison software or algorithms such as a BLAST search of SNP databases. Additionally, the present invention provides methodologies useful in the selection of intragenic SNPs for genotyping in genetic studies.

BACKGROUND OF THE INVENTION

The identification and analysis of a particular gene or protein, or of a single nucleotide polymorphism (SNP), has generally been accomplished by experiments directed specifically towards that gene or protein, or SNP. With the recent advances, however, in the sequencing of the human genome, the challenge is to decipher the expression, function, and regulation of thousands of genes that can contain intragenic SNPs, which cannot be realistically accomplished by analyzing one gene or protein, or SNP at a time. To address this situation, the data mining methodologies of the present invention have been developed and proven to be a valuable tool.

Information is accumulating about the normal variation among human genomes. During the course of evolution, spontaneous mutations appear in the genomes of organisms. Variations in genomic DNA sequences have been estimated as being created continuously at a rate of about 100 new single base changes per individual. Kondrashow, 175 THEOR. BIOL. 583-94 (1995); Crow, 12 EXP. CLIN. IMMUNOGENET. 121-28 (1995). These changes in the progenitor nucleotide sequences can confer an evolutionary advantage that likely increases the frequency of the mutation, an evolutionary disadvantage that likely decreases the frequency of the mutation, or the mutation will be neutral. In many cases, equilibrium is established between the progenitor and mutant sequences so that both are present in the population. The presence of both forms of the sequence results in genetic variation or polymorphism. Over time, a significant number of mutations can accumulate within a population such that considerable polymorphism can exist between individuals within the population.

Numerous types of polymorphisms are known to exist. There are several sources of sequence variation, such as when DNA sequences are either inserted or deleted from the genome, for example, by viral insertion. The presence of repeated sequences in the genome can also cause sequence variation and is variously termed short tandem repeats (STRs), variable number tandem repeats (VNTRs), short sequence repeats (SSRs) or microsatellites. These repeats can be dinucleotide, trinucleotide, tetranucleotide, or pentanucleotide repeats. Polymorphism results from variation in the number of repeated sequences found at a particular locus.

Most commonly, sequence differences between individuals involve differences in single nucleotide positions. SNPs account for approximately 90% of human DNA polymorphism. Collins et al., 8 GENOME RES. 1229-31 (1998). SNPs include single base pair positions in genomic DNA at which different sequence alternatives (alleles) exist in a population. In addition, the least frequent allele generally must occur at a frequency of 1% or greater. DNA sequence variants with a reasonably high population frequency are observed approximately every 1,000 nucleotide across the genome, with estimates as high as 1 SNP per 350 base pairs. Wang et al., 280 SCIENCE 1077-82 (1998); Harding et al., 60 AM. J. HUMAN GENET. 772-89 (1997); Taillon-Miller et al., 8 GENOME RES. 748-54 (1998); Cargill et al., 22 Nat. GENET. 231-38 (1999); and Semple et al., 16 BIOINFORM. DISC. NOTE 735-38 (2000). The frequency of SNPs varies with the type and location of the change. In base substitutions, two-thirds of the substitutions involve the C-T and G-A type. This variation in frequency can be related to 5-methylcytosine deamination reactions that occur frequently, particularly at CpG dinucleotides. Regarding location, SNPs occur at a much higher frequency in non-coding regions than in coding regions. Information on over one million variable sequences is already publicly available via the Internet and more such markers are available from commercial providers of genetic information. Kwok and Gu, 5 MED. TODAY 538-53 (1999).

Several definitions of SNPs exist. See, e.g., Brooks, 235 GENE 177-86 (1999). As used herein, the term "single nucleotide polymorphism" or "SNP" includes all single base variants, thus including nucleotide insertions and deletions in addition to single nucleotide substitutions. There are two types of nucleotide substitutions. A transition is the replacement of one purine by another purine or one pyrimidine by another pyrimidine. A transversion is the replacement of a purine for a pyrimidine, or vice versa.

The inheritance patterns of most common diseases are complex, indicating that the diseases are probably caused by mutations in one or more genes and/or through interactions between genes and environment. Many known human DNA sequence variants are known to be associated with particular diseases or to influence an individual's response to a particular drug. See, e.g., Drysdale et al., 12 PROC. NAT. ACAD. SCI. 10483-84 (2000). Because of the high frequency of SNPs within the genome, there is a greater probability that a SNP will be linked to a genetic locus of interest than other types of genetic markers.

Numerous methods exist for detecting SNPs within a nucleotide sequence. A review of many of these methods can be found in Landegren et al., 8 GENOME RES. 769-76 (1998). For example, a SNP in a genomic sample can be detected by preparing a Reduced Complexity Genome (RCG) from the genomic sample, then analyzing the RCG for the presence or absence of a SNP. See, e.g., WO 00/18960. Multiple SNPs in a population of target polynucleotides in parallel can be detected using, for example, the methods of WO 00/50869. Other SNP detection methods include the methods of U.S. Pat. Nos. 6,297,018 and 6,322,980. Furthermore, SNPs can be detected by restriction fragment length polymorphism (RFLP) analysis. See, e.g., U.S. Pat. Nos. 5,324,631; 5,645,995. RFLP analysis of SNPs, however, is limited to cases where the SNP either creates or destroys a restriction enzyme cleavage site. SNPs can also be detected by direct sequencing of the nucleotide sequence of interest. In addition, numerous assays based on hybridization have also been developed to detect SNPs and mismatch distinction by polymerases and ligases.

SNPs can be a powerful tool for the detection of individuals whose genetic make-up alters their susceptibility and/or predisposition to certain diseases. Genotyping of such markers therefore can be valuable to characterize patient populations.

DNA sequence variants with no known functional consequences can also be useful in association and linking analyses. For example, information may be revealed that can then be used to detect individuals at risk for pathological conditions based on the presence of SNPs.

SNPs can be directly or indirectly associated with disease conditions in humans or animals. In a direct association, the alteration in the genetic code caused by the SNP directly results in the disease condition. Sickle cell anemia and cystic fibrosis are examples of direct SNP association with a disease. In an indirect association, the SNP does not directly cause the disease, but may alter the physiological environment such that there is an increased likelihood that the patient is susceptible to develop the disease as compared to an individual without the SNP. Additionally, SNPs can also be associated with disease conditions, without a direct or an indirect association with the disease. In this case, the SNP may be located in close proximity to the defective gene, usually within 5 centimorgans, such that there is a strong association between the presence of the SNP and the disease state.

Disease-associated SNPs can occur in coding and non-coding regions of the genome. When located in a coding region, a SNP can result in the production of a protein that is non-functional or that has decreased functionality. More frequently, SNPs may occur in non-coding regions. If a SNP occurs in a regulatory region, it can affect expression of the protein. For example, the presence of a SNP in a promoter region can alter the expression of a protein. If the protein is involved in protecting the body against development of a pathological condition, this decreased expression can make the individual more susceptible to the condition.

In association studies, the frequency of variants of individual genetic markers are compared between healthy persons and patient populations, anticipating that an observed difference in frequency can be the direct effect of the sequence difference. Also, co-inheritance with nearby unknown genetic variants can have such an effect. Associated markers with no direct effect on disease are referred to as being in linkage disequilibrium with the disease-related changes. Chapman and Thompson, 42 ADV. GENET. 413-37 (2001). These variants may, therefore, provide a guide to the gene that is directly involved in the disease. If the DNA sequence is derived from an individual in families where the particular disease is known to segregate, then the location of the disease-associated genetic changes among the chromosomes can be pinpointed by genetic linkage analysis, using the same types of genetic markers. This methodology has proven valuable for defining the nature of conditions primarily influenced by single or a limited number of genes. See, e.g., Alizadeh et al., 403 NATURE 503-11 (2000).

SNPs are well-suited for identifying genotypes that predispose an individual to develop a disease condition for several reasons. First, SNPs are the most common polymorphisms present in the genome, and are frequently located in or near any locus of interest. Because SNPs located in genes can be expected to directly affect protein structure or expression levels, they not only serve as markers but also as candidates for gene therapy treatments to cure or prevent a disease. SNPs also show greater genetic stability than repeated sequences and thus are less likely to undergo changes that would complicate diagnosis.

In particular diseases, single or small sets of genes have been identified that are typically altered by mutations. The identification of such disease-genes and their associated SNPs provides insights into the causes of common diseases and promotes the development of highly specific diagnostic and therapeutic products. Identifying and characterizing candidate genes and SNPs is critical for defining disease pathways, disease stages, drug effect pathways, and drug metabolic pathways. Sequence variation, as it relates to drug response, can aid in predicting the safety, toxicity, and/or efficacy of drugs. Along these lines, correlating SNPs with drug effects, therapy, and clinical outcome can significantly improve productivity and increase the efficiency of the development or improvement of drugs. Besides advancing drug development, SNPs can further facilitate developments in and improvements of methods and products, such as gene and antisense therapies, molecular diagnostics for predicting drug responses, and molecular diagnostics for selecting drug dosing regimens based upon genotype.

The increased efficiency of SNP detection methods makes them especially suitable for high-throughput typing systems, which are necessary to screen large populations. Information about hundreds of pathologic alterations that have been observed are already archived in mutation databases, some of which are available via the Internet. By taking advantage of the sequence information obtained from such databases, the successful application of large-scale biological analyses for annotating thousands of SNPs in genomic and cDNA sequences provides for the better understanding of the association of SNPs to a pathological condition. The data mining methodology of the present invention promises new opportunities in genetic research, thus adding value to the existing and forthcoming large-scale projects aiming to discover sequence variations in the human and other genomes. With these tools, the increasing number of publicly or privately available SNPs can be validated and assessed for their intragenic context and redundancy. The data mining methodology of the present invention is useful in the selection process of intragenic SNPs, thus providing a new tool for genotyping in genetic studies, which are effective for establishing the research, diagnostic, and treatment value of SNPs.

Implementing high-throughput SNP genotyping as a tool in genetic research projects preferably requires the availability of databases comprising high quality annotation data on known SNPs. Such resources are especially important when the selection of SNPs assayed in a genotyping facility is based upon SNP database information. Indeed, high quality SNP annotation avoids costly SNP assay development and genotyping of SNPs that later turn out to be invalid SNPs or not located at the expected chromosomal region. The methodology of the present invention also can filter out SNPs that map within regions of repeat sequences thus discarding a number of intragenic SNPs annotated by other SNP databases that are typically less relevant for genotyping purposes.

Following annotation by the methods of the present invention, the genetic context and redundancy of the SNPs can be efficiently and effectively assessed. The nucleotide sequences searched by the methods of the present invention, and annotated SNP IDs, can be matched and the genomic region defined, e.g., by repeat, promoter, coding sequence, and so forth. This data mining methodology can reveal additional and high quality SNPs compared to the SNPs that are annotated by the respective databases. Among the other advantages, the data mining methodology of the present invention can prevent problems arising in case of short flanking regions in the databases. Thus, this new technology offers a more effective tool in the process of selecting validated intragenic SNPs from databases that, for example, can be used in candidate gene association studies and for linkage analysis.

SUMMARY OF THE INVENTION

The present invention relates to data mining of SNP databases for the selection of intragenic SNPs. The present invention provides methodologies for annotating SNPs onto candidate genes based on, in one embodiment, a BLAST search of SNP databases. Additionally, the present invention provides methodologies useful in the selection of intragenic SNPs for genotyping in genetic studies.

In one embodiment of the present invention, the method for annotating SNPs onto candidate nucleic acid sequences comprises the steps of generating subsequences of nucleic acid from the candidate nucleic acid sequence, comparing each of the subsequences against one or more SNP databases to obtain relevant SNP output files, analyzing the relevant SNP output files for relevant valid SNPs, and annotating the relevant valid SNPs. The nucleic acid of the present invention can comprise gDNA, cDNA, and mRNA.

With regard to this annotation method, the present invention comprises comparing the relevant valid SNPs against a database, such as the REPBASE database, and discarding the relevant valid SNPs located within repeat regions of the candidate nucleic acid sequence. In a specific embodiment, this comparison can be performed using an expectation value upper limit of about $10^{-3}$.

In another embodiment of the present invention, this annotation method further comprises recalculating the nucleic acid positions for the relevant valid SNPs in the candidate nucleic acid sequence.

In one embodiment of the present invention, the nucleic acid subsequences comprise a length between about 1000 bp to about 5000 bp. Further, the nucleic acid subsequences can have an overlap of nucleic acid sequence between flanking sequences within the range of about 100 bp to about 500 bp. In a specific embodiment of the present invention, the nucleic acid subsequences comprise a length of about 1500 bp. In another specific embodiment of the present invention, the nucleic acid subsequences can have an overlap of about 250 bp between flanking regions.

In a specific embodiment of the present invention, the nucleic subsequences can be compared against the SNP databases by utilizing the BLAST program. With regard to this BLAST comparison, the present invention provides the generation of BLAST output files. In this regard, the BLAST output files can be analyzed for validation of the relevant SNPs. In a more specific embodiment of the present invention, the validation of relevant SNPs comprises applying the following criteria: the SNP location is within boundaries of the hit length, the expectation value is at least about $10^{-12}$ or below, the minimum identity is about 98% or greater between the SNP hit and the query sequence, and the hit length is at least about 250 bp or longer.

In another specific embodiment of the present invention, the validating of relevant SNPs comprises applying the following criteria: the SNP location is within boundaries of the hit length, the expectation value is at least about $10^{-12}$ or below, the minimum identity is about 98% or greater between SNP hit and query sequence, and the hit length equals at least about 98% of the length of SNP entry in the one or more SNP databases.

In one embodiment, the present invention also provides a computer data based search engine that can be utilized to obtain additional information regarding the relevant valid SNPs. With regard to this method, the additional information can be selected from a compound, gene, cell, virus, sequence, and substance that affect the relevant valid SNP.

A further aspect of the present invention comprises annotating relevant valid SNPs. In a particular aspect of the present invention annotating can comprise assigning the relevant valid SNP to a gene location. Further yet, annotating can comprise assigning a gene name to the relevant valid SNPs. The SNP can be assigned to a gene position comprising the 5'UTR, promoter region, nucleic acid coding region, 3'UTR, and introns.

Yet another embodiment of the present invention provides a system for annotating SNPs onto candidate nucleic acid sequences comprising the steps of generating subsequences of nucleic acid from the candidate nucleic acid sequence, comparing each of the subsequences against one or more SNP databases to obtain relevant SNP output files, analyzing the relevant SNP output files for relevant valid SNPs, annotating the relevant valid SNPs, and recalculating nucleic acid positions for the relevant valid SNPs in the candidate nucleic acid sequence. With regard to this annotation method, a further aspect comprises displaying the relevant valid SNPs on a computer readable medium.

In a specific embodiment, the present invention also provides a computer-implemented method for annotating SNPs onto candidate nucleic acid sequences comprising the steps of generating subsequences of nucleic acid from the candidate nucleic acid sequence, comparing each of the subsequences against one or more SNP databases to obtain relevant SNP output files, analyzing the relevant SNP output files for relevant valid SNPs, annotating the relevant valid SNPs, and recalculating nucleic acid positions for the relevant valid SNPs in the candidate nucleic acid sequence.

Yet another specific embodiment of the present invention provides a computer-implemented system for annotating SNPs onto candidate nucleic acid sequences comprising the steps of importing or having stored nucleic acid sequence data information from one or more databases, generating relevant SNP output files by comparing nucleic acid subsequences obtained from candidate nucleic acid sequence against the one or more databases using BLAST, storing the relevant SNP output files analyzing the relevant SNP output files based on stored criteria for relevant valid SNPs, annotating the relevant valid SNPs, and recalculating nucleic acid positions for the relevant valid SNPs in the candidate nucleic acid sequence. With regard to this computer-implemented aspect of the present invention, the method comprises discarding the relevant valid SNPs located within repeat regions of the candidate nucleic acid sequence. In a specific aspect, the criteria of the computer-implemented system comprise at least one of at least about 98% identity, BLAST hit length covering at least about 98% of the length of SNP entry in the one or more databases, or is longer than about 250 bp, and location in non-repetitive DNA.

A further specific embodiment of the present invention provides a method for determining an association between a SNP and a pathological condition comprising the steps of: importing or having stored nucleic acid sequence data information from one or more databases, generating relevant SNP output files by comparing nucleic acid subsequences obtained from candidate nucleic acid sequence against the one or more databases using BLAST, storing the relevant SNP output files, analyzing the relevant SNP output files based on stored criteria for relevant valid SNPs, annotating the relevant valid SNPs, and recalculating nucleic acid positions for the relevant valid SNPs in the candidate nucleic acid sequence.

Yet another specific embodiment of the present invention provides a method for determining an association between a SNP and a pathological condition comprising the steps of: generating subsequences of nucleic acid from the candidate nucleic acid sequence, comparing each of the subsequences against one or more SNP databases to obtain relevant SNP output files, analyzing the relevant SNP output files for relevant valid SNPs, and annotating the relevant valid SNPs.

An alternative specific embodiment of the present invention provides a method for determining an association between a SNP and a drug response comprising the steps of: importing or having stored nucleic acid sequence data information from one or more databases, generating relevant SNP output files by comparing nucleic acid subsequences obtained from candidate nucleic acid sequences against the one or more databases using BLAST, storing the relevant SNP output files, analyzing the relevant SNP output files based on stored criteria for relevant valid SNPs, annotating the relevant valid SNPs, and recalculating nucleic acid positions for the relevant valid SNPs in the candidate nucleic acid sequence.

Yet another alternative specific embodiment of the present invention provides a method for determining an association between a SNP and a drug response comprising the steps of: generating subsequences of nucleic acid from the candidate nucleic acid sequence, comparing each of the subsequences against one or more SNP databases to obtain relevant SNP output files, analyzing the relevant SNP output files for relevant valid SNPs, and annotating the relevant valid SNPs.

BRIEF DESCRIPTION OF THE DRAWINGS

FIG. 6 provides a list of the 24 genes used in one embodiment of the methods of the present invention, indicating the location of the gene on the Human Genome Working Draft sequence (Dec. 12, 2000 Freeze), the mRNA Genbank Accession number, and the OMIM Reference number.

FIG. 7 provides the total length of each genomic region and the length of the non-repetitive DNA in this region for the 24 genes analyzed.

FIG. 8 provides an overview of number of SNPs per gene as annotated by the present invention, grouped by database source and genomic region. The right columns display the number of SNPs after merging of the data from dbSNP and HGBASE. These numbers do not include SNPs located in repeat regions.

DETAILED DESCRIPTION OF THE INVENTION

Figure 1:
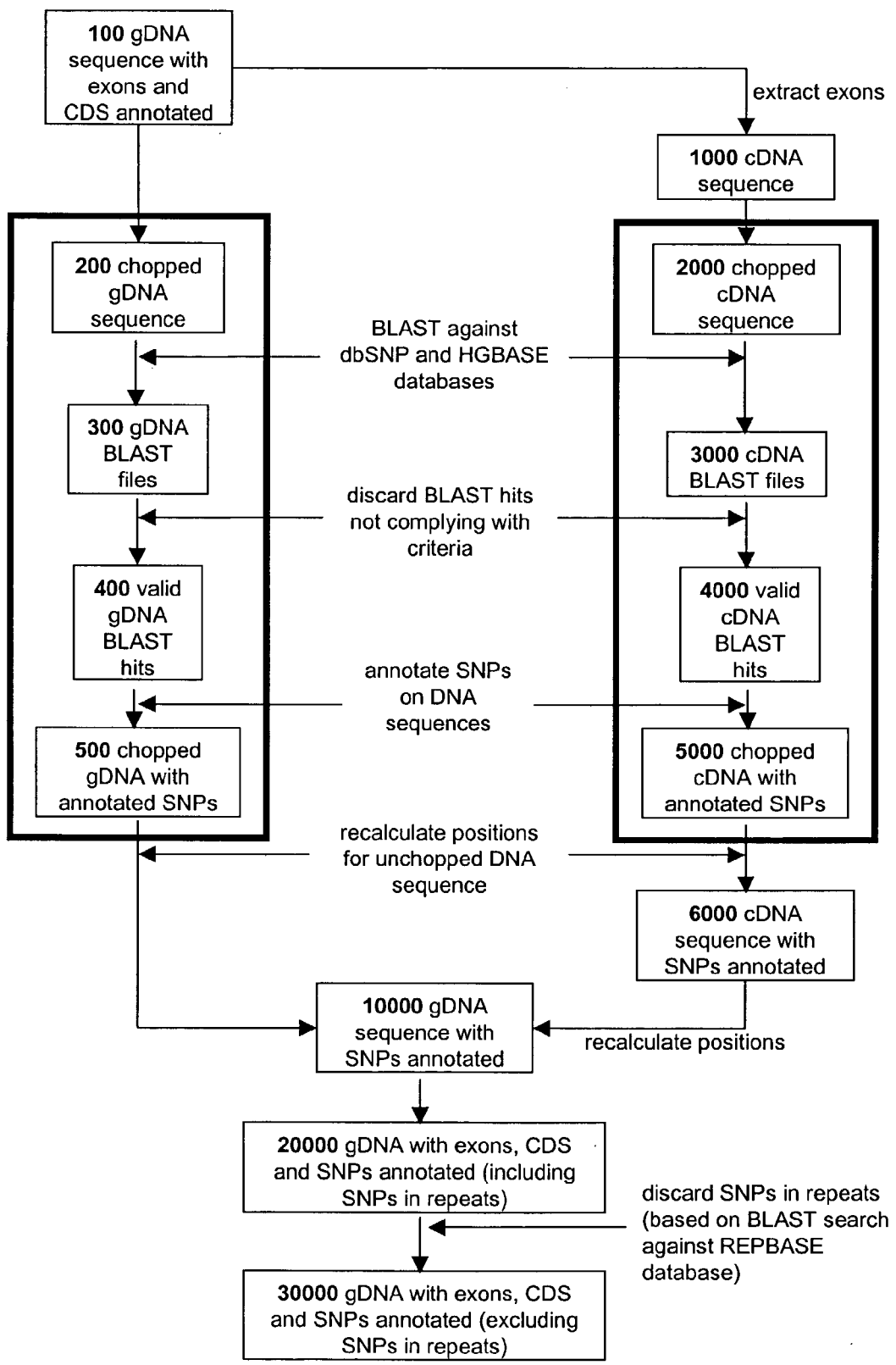
FIG. 1 provides a schematic overview of one embodiment of the methods of the present invention utilizing the BLAST program. Criteria used to retain a BLAST hit: (1) the actual SNP is located in the BLAST hit; (2) a minimum of about 98% identity between SNP hit and query sequence; and (3) the hit length exceeds 250 by or, alternatively, equals a minimum of about 98% of the context length of that SNP in the public SNP database. The bold numbers in each box are numeric labels that represent the various steps in the flow chart.

It is understood that the present invention is not limited to the particular methodology, databases, gene sequences, SNPs, and gene sequence analysis method, etc., described herein, as these can vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a SNP" is a reference to one or more SNPs and includes equivalents thereof known to those skilled in the art and so forth. Indeed, one skilled in the art can use the methods described herein to annotate any valid SNP (known presently or subsequently) present in any database.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the methods, devices and materials are now described.

All publications and patents mentioned herein are hereby incorporated by reference for the purpose of describing and disclosing, for example, the constructs and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

For convenience, the meaning of certain terms and phrases employed in the specification, examples, and appended claims are provided below. The definitions are not meant to be limiting in nature and serve to provide a clearer understanding of certain aspects of the present invention.

nt=nucleotide
bp=base pair
kb=kilobase; 1000 base pairs
SNP=single nucleotide polymorphism
HGBASE=Human Genic Bi-Allelic Sequence database
HGVbase=Human Genome Variation database
gDNA=genomic DNA The term "genome" is intended to include the entire DNA complement of an organism, including the nuclear DNA component, chromosomal or extrachromosomal DNA, as well as the cytoplasmic domain (e.g., mitochondrial DNA).

The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers can be single or double-stranded. However, linkages can include any of the linkages known in the art including, for example, nucleic acids comprising 5' to 3' linkages. The nucleotides can be naturally occurring or can be synthetically produced analogs that are capable of forming base-pair relationships with naturally occurring base pairs. Examples of non-naturally occurring bases that are capable of forming base-pairing relationships include, but are not limited to, aza- and deaza-pyrimidine analogs, aza- and deaza-purine analogs, and other heterocyclic base analogs, wherein one or more of the carbon and nitrogen atoms of the pyrimidine rings have been substituted by heteroatoms, e.g., oxygen, sulfur, selenium, phosphorus, and the like. Furthermore, the term "nucleic acid sequences" contemplates the complementary sequence and specifically includes any nucleic acid sequence that is substantially homologous to both the nucleic acid sequence and its complement.

"Polynucleotide" refers to a linear polymer of at least 2 nucleotides joined together by phosphodiester bonds and can comprise of either ribonucleotides or deoxyribonucleotides.

"Sequence" means the linear order in which monomers occur in a polymer, for example, the order of amino acids in a polypeptide or in the order of nucleotides in a polynucleotide.

"Polymorphism" refers to a set of genetic variants at a particular genetic locus among individuals in a population.

"Promoter" means a regulatory sequence of DNA that is involved in the binding of RNA polymerase to initiate transcription of a gene. A "gene" is a segment of DNA involved in producing a peptide, polypeptide, or protein, including the coding region, non-coding regions preceding ("5'UTR") and following ("3'UTR") the coding region, as well as intervening non-coding sequences ("introns") between individual coding segments ("exons"). A promoter is herein considered as a part of the corresponding gene. Coding refers to the representation of amino acids, and start and stop signals in a three base "triplet" code. Promoters are often upstream ("5'to") the transcription initiation site of the gene.

A "candidate gene" or "target gene" refers to a nucleic acid, often derived from a biological sample, on which one or more SNPs specifically reside and to which BLAST searches share at least about 95% identity with the candidate or target sequence.

"Wild type allele" means the most frequently encountered allele of a given nucleotide sequence.

As used herein, "allele frequency" means the frequency that a given allele appears in a population.

"Genetic variant" or "variant" means a specific genetic variant which is present at a particular genetic locus in at least one individual in a population and that differs from the wild type.

The terms "genetic predisposition," "genetic susceptibility," and "susceptibility" all refer to the likelihood that an individual subject will develop a particular disease, condition or disorder. For example, a subject with an increased susceptibility or predisposition will be more likely than average to develop a disease, while a subject with a decreased predisposition will be less likely than average to develop the disease. A genetic variant is associated with an altered susceptibility or predisposition if the allele frequency of the genetic variant in a population or subpopulation with a disease, condition or disorder varies from its allele frequency in the population without the disease, condition or disorder (control population) or a control sequence (wild type).

"Gene therapy" means the introduction of a functional gene or genes from some source by any suitable means into a living cell to correct for a genetic defect.

The term "biological sample" refers to a sample obtained from an organism (e.g., patient) or from components (e.g., cells) of an organism. The sample can be of any biological tissue or fluid. The sample can be a "clinical sample" which is a sample derived from a patient. Such samples include, but are not limited to, sputum, blood, blood cells (e.g., white cells), amniotic fluid, plasma, semen, bone marrow, tissue or fine needle biopsy samples, urine, peritoneal fluid, and pleural fluid, or cells therefrom. Biological samples can also include sections of tissues such as frozen sections taken for histological purposes. A biological sample can also be referred to as a "patient sample."

As used herein, the terms "patient" and "subject" are not limited to human beings, but are intended to include all vertebrate animals in addition to human beings.

"Expectation" value as used herein refers to the statistical significance threshold for reporting matches against database sequences.

As a result of large-scale projects aiming to discover sequence variations in the human genome, the number of publicly available SNPs has increased enormously over the past few years, and offers new opportunities in genetic research. A high abundance of genetic markers, in casu SNPs, facilitate association studies on complex multifactorial diseases, both based on single SNPs and haplotypes. Lander et al., 265 SCIENCE 2037-48 (1994); Gray et al., 9 HUM. MOL. GENET. 2403-08 (2000); Kao et al., 29 ANN. ACAD. MED. SINGAPORE 376-82 (2000); Johnson et al., 29 NAT. GENET. 233-37 (2001).

Several SNP databases exist, among which the public dbSNP and HGBASE are the largest, together comprising several millions SNPs. They include the following: http://www.ncbi.nlm.nih.gov/SNP/; ftp://ftp.ncbi.nlm.nih.gov/snp/human/rs_fasta/ (dbSNP); http://hgbase.cgr.ki.se; ftp://ftp.ebi.ac.uk/pub/databases/variantdbs/hgbase/ (HGBASE); http://hgvbase.cgb.ki.se (HGVBASE); http://genome.ucsc.edu (Human Genome Project Working Draft); http://www.girinst.org (REPBASE); and http://www.imm.ki.se/CYPalleles/cyp2a6.htm (CYP2A6).

The dbSNP database is a central repository for newly discovered genomic and cDNA sequence variations, both single base changes and short deletions and insertions, from any species. Sherry et al., 29 NUCL. ACIDS RES. 308-11 (2001). The Human Genic Bi-Allelic SEquences (HGBASE) database is gene-oriented: it supports the candidate gene association study principle and is therefore a catalog of intragenic sequence variants. Brookes et al., 28 NUCL. ACIDS RES. 356-60 (2000). The HGBASE database has adopted the name HGVbase (Human Genome Variation database). For each SNP entry, these databases comprise at least a unique accession number, the nucleotide variation, and the sequence context of the SNP. When available, additional information is provided, such as the chromosomal location, the gene that comprises the SNP, the effect of a SNP on the amino acid sequence of an encoded protein, the allele frequencies in different ethnic populations and/or the methods of assay and discovery. Accordingly, these databases represent a highly valuable source of information for selecting SNPs that can be analyzed in a genotyping facility.

A prerequisite for implementing high-throughput SNP genotyping as a tool in genetic research projects is the availability of reliable databases comprising high quality annotation data on known SNPs. For genotyping and assay development, in particular, such a resource is especially important when SNPs are being selected based on SNP database information rather than on more expensive in house SNP discovery studies. Obviously, the SNP annotation quality in such databases should be high to avoid costly SNP assay development and genotyping of SNPs that later turn out to be invalid or located at a different region than to which the database annotated.

For the foregoing reasons, the present invention provides data mining methodologies for annotating intragenic SNPs to specified genes. In a specific embodiment, the present invention utilizes the BLAST algorithm and predefined criteria to select valid SNPs from databases, such as the dbSNP and HGBASE databases. Nonetheless, any appropriate sequence comparison software or algorithms can be used in the context of the methods of the present invention.

In one embodiment, the methods of the present invention contemplate four main steps for analyzing and annotating SNPs onto a candidate gene. First, a candidate nucleic acid sequence is chopped into subsequences. Second, the nucleic acid subsequences are blasted against a SNP database. Third, hits that do not comply with predefined criteria are discarded from further analysis. Fourth, the relevant valid SNPs are annotated onto the nucleic acid sequence. The methods of the present invention further comprise recalculating nucleic acid positions for the relevant valid SNPs in the candidate nucleic acid sequence. Further, the present invention also comprises filtering out SNPs in repeats, thus discarding those from further analysis.

As a first step, the candidate genomic or cDNA nucleic acid sequence is chopped into subsequences. In one embodiment, the candidate nucleic acid sequence can be chopped into subsequences of about 1000 bp to about 5000 bp. The subsequences can overlap between flanking sequences and, in one embodiment, within a range from about 100 bp to about 500 bp. In a specific embodiment of the present invention, the subsequences are about 1500 bp with an overlap of about 250 bp between flanking sequences.

As a second step, the candidate genomic or cDNA sequence can be blasted against one or more SNP databases in one embodiment. Although BLAST can be used, this invention is not so limited and any appropriate software sequence comparison method or algorithms can be used as part of the data mining methodology of the present invention. In a specific embodiment, the databases are the downloaded dbSNP and HGBASE.

The methods of the present invention illustrate that genomic DNA is the most valuable sequence for searching databases using BLAST, both for dbSNP and HGBASE. The cDNA, however, is still a valuable source for blasting HGBASE, particularly when the genomic DNA sequence is not available. More specifically, four out of five SNPs that were found in HGBASE were identified using the cDNA sequence only. Both the gDNA and cDNA sequences were chopped into smaller subsequences before they were blasted. Because the BLAST algorithm was originally designed to search for amino acid sequences, it is not best suited to process large sequences. More specifically, the algorithm aims to spread its hits over the full length of the queried sequence. Thus, it likely reports less relevant hits that are located in an area with fewer SNPs over more relevant hits in a region with many SNPs. In one embodiment, the present invention's data mining methods of chopping the query sequence in smaller parts (e.g., about 1500 bp), which increases the number of BLAST hits that will return, can circumvent this problem.

In a third step, hits that do not comply with predefined criteria are discarded from further analysis. In one embodiment, the criteria for validating the BLAST hits can be one of percentage identity, BLAST hit length in percentage or BLAST hit length longer than about 250 bp, and/or location in non-repetitive DNA. In a specific embodiment, the hit can comply with a minimum of about 98% identity, the BLAST hit length covering at least about 98% of the length of the SNP entry in the database or is longer than about 250 bp, and is located in non-repetitive DNA.

Accordingly, one aspect of the present invention contemplates using the parameter "relative BLAST hit length," as a selection criterion to reduce the chances of erroneous annotation. The parameter may use a threshold of about 98%, which essentially prevents BLAST hits that have a high percentage identity but include only a (small) part of the SNP database entry to be accepted as valid SNPs. This threshold, however, may not be used for BLAST hits longer than 250 bp, because SNPs that are mapped in the overlapping region of two subsequences may not intrinsically reach this threshold. Thus, BLAST hits longer than 250 nucleotides are accepted when the other criteria are fulfilled because a hit longer than 250 nucleotides provides some assurance that the SNP's flanking regions are mapped to the correct genomic or cDNA sequence. This can be an issue, however, with highly homologous genes or pseudogenes. To further reduce the chance that the latter issue would arise (e.g., in a gene known to be a member of a large gene family), the length of the overlapping subsequence can be increased (e.g., to about 500 bp or more instead of about 250 bp). This allows for a more stringent criterion on the BLAST hit length. Accordingly, the hit length may exceed about 98% of the database SNP entry length (as before), unless it is longer than 500 bp. The 98% threshold value can be chosen because it likely results in high quality data. Indeed, less stringent threshold values (e.g., about 95% or about 96/97%) would lead to very similar results and are also contemplated.

In a fourth step, the relevant valid SNPs can be annotated onto the nucleic acid sequence. Further, one embodiment the present invention provides that the outcomes of the individual BLAST analysis of each of the chopped subsequences can be integrated into the candidate cDNA or genomic nucleic acid sequence by recalculating nucleic acid positions for the relevant valid SNPs in the candidate nucleic acid. In another embodiment, as a final step the SNPs that mapped into regions of repeat sequences can be filtered out. This can be desirable because such SNPs are usually less relevant to be selected for genotyping purposes.

The methods of the present invention provide two aspects of data mining analysis. One involves validating the SNPs that are already annotated within publicly or privately available SNP databases. Specifically, this analysis is designed to exclude the SNPs that have been erroneously annotated within such SNP databases. Another analysis can involve identifying SNPs that have not been annotated within the SNP databases.

Performing the methods of the present invention on the public SNP databases HGBASE and dbSNP revealed that their SNP content are not only highly complementary, but also overlap significantly. It may not be sufficient to search only one of these databases in order to identify every single intragenic SNPs in a candidate gene. Moreover, when available, other gene specific mutation databases or literature can also contain additional information on mutations or SNPs in the candidate gene. In one embodiment, the present invention also provides a computer data based search engine that can be utilized to obtain additional information regarding the relevant valid SNPs. With regard to this method, the additional information can be selected from a compound, gene, cell, virus, sequence, and substance that affect the relevant valid SNP.

The combined analysis of dbSNP and HGBASE yielded SNP densities in the same order of magnitude as the most often quoted figure of 1 SNP per 1000 bp, with estimates as high as 1 SNP per 350 bp. Taillon-Miller et al. (1998); Cargill et al. (1999); and Semple et al. (2000). Interestingly, the in silico SNP density is higher in the coding regions than in the intronic regions. This can be attributed to the fact that many SNPs have been identified by alignment of EST sequences, resulting in an artificial increase of the number of SNPs found in coding regions.

The present invention provides methodologies for annotating relevant valid SNPs onto a candidate nucleic acid sequence. In one embodiment, annotating can refer to assigning a relevant valid SNP to a gene name location, or determining an association of a SNP with a pathological condition or drug response. Further, SNP annotation can include allele frequencies, information based on association of SNP with gene function, and documentation of the source population, such as size and geographical location. The SNP can be located within the promoter region, the 5'UTR, the coding sequence, the intron region, or the 3'UTR. Further, the relevant valid SNP can be located within a non-repeat region.

In one specific embodiment, gDNA chopped sequences can be used in the context of the methods of the present invention. As noted in block 100 of FIG. 1, a gDNA sequence with exons and CDS annotated can be used as the candidate nucleic acid. Then the chopped gDNA sequence 200 can be blasted against dbSNP and HGBASE databases for creating the gDNA BLAST files 300, although any appropriate software or algorithms and any SNP database can also be used. The algorithm discards BLAST hits not complying with criteria and the SNPs on the remaining valid gDNA BLAST hits 400 are annotated, generating the chopped gDNA sequence with annotated SNPs 500. The nucleic acid positions for the validated SNPs that are annotated onto the chopped gDNA sequence 500 can then be recalculated to correspond to an unchopped gDNA sequence, generating gDNA sequence 10000 with the SNPs annotated. Further, the gDNA sequence 20000 has exons, CDS, and SNPs annotated, including SNPs in repeats. Thus, a BLAST search against, for example, the REPBASE database generates the gDNA sequence 30000, with exons, CDS, and SNPs annotated, and which excludes SNPs in repeats.

In another specific embodiment, cDNA chopped sequences can be used in the context of the methods of the present invention. As noted in block 1000 of FIG. 1, after having extracted exons from the gDNA sequence 100, a cDNA sequence can be used as the candidate nucleic acid. The chopped cDNA sequence 2000 can be blasted against dbSNP and HGBASE databases for creating the cDNA BLAST files 3000, although any appropriate software or algorithms and any SNP database can also used. The algorithm discards BLAST hits not complying with criteria and the SNPs on the remaining valid cDNA BLAST hits 4000 are annotated, generating the chopped cDNA sequence 5000. The nucleic acid positions for the validated SNPs that are annotated onto the chopped cDNA sequence 5000 can then be recalculated to correspond to an unchopped cDNA sequence, generating cDNA sequence 6000 with the SNPs annotated. The nucleic acid positions for the SNPs that are annotated onto cDNA sequence 6000 can then be recalculated to correspond to the gDNA sequence, generating gDNA sequence 10000 with the SNPs annotated. Further, the gDNA sequence 20000 has exons, CDS, and SNPs annotated, including SNPs in repeats. Thus, a BLAST search against, for example, the REPBASE database generates the gDNA sequence 30000, with exons, CDS, and SNPs annotated, and which excludes SNPs in repeats.

In one embodiment of the present invention, the candidate nucleic acid sequence can be DNA or RNA. For the analysis of genomic DNA, virtually any biological sample containing genomic DNA can be used. For example, and without limitation, genomic DNA can be conveniently obtained from whole blood, semen, saliva, tears, urine, fecal material, sweat, buccal cells, skin, or hair. For assays using cDNA or mRNA, the candidate nucleic acid can be obtained from cells or tissues that express the candidate nucleic acid sequence. Further, one embodiment of the present invention provides a method for determining an association of a SNP to a pathological condition. In this method a biological sample is obtained from a subject. The subject can be a human being or any vertebrate animal. The biological sample can contain polynucleotides and preferably genomic DNA. The form of the polynucleotide is not critically important such that the use of cDNA, DNA, RNA, or mRNA is contemplated within the scope of the method. The polynucleotide can be analyzed for SNPs by the data mining methodology of the present invention, wherein such a SNP is associated with, for example, a pathological condition.

In another embodiment the present invention provides a method for determining an association of a SNP to a specific drug response. The subject can be a human being or any vertebrate animal. The biological sample can contain polynucleotides and preferably genomic DNA. The form of the polynucleotide is not critically important such that the use of cDNA, DNA, RNA, or mRNA is contemplated within the scope of the method. The polynucleotide can be analyzed for SNPs by the data mining methodology of the present invention, wherein such a SNP is associated with a drug response.

In a further embodiment of the present invention, the information gained from the methods of the present invention can be used to design treatment regimens, such as gene therapy or drug treatment regimens.

SNP Data Mining Database

The SNP data mining database can be an internal database designed to include annotation information about the SNPs generated by the methods of the present invention. Such information can include, for example, the databases in which a given nucleic acid sequence onto which relevant valid SNPs were found, descriptive information about related gDNA, cDNA, or mRNA associated with the sequence, tissue or cell source, sequence data obtained from external sources, and preparation methods. The database can be divided into two sections: one for storing the sequences and the other for storing the associated information. This database can be maintained as a private database with a firewall within the central computer facility. However, this invention is not so limited and the SNP Data Mining database can be made available to the public.

The database can be a network system connecting the network server with users. The network can be any one of a number of conventional network systems, including a local area network (LAN) or a wide area network (WAN), as is known in the art (e.g., Ethernet). The server can include software to access database information for processing user requests, and to provide an interface for serving information to user machines. The server can support the World Wide Web and maintain a website and Web browser for user use. User/server environments, database servers, and networks are well documented in the technical, trade, and patent literature.

Through a Web browser, users can construct search requests for retrieving data from a SNP Data Mining database. A user can in addition construct requests for retrieving data from one or more SNP databases. These SNP databases can be public, such as dbSNP and HGBASE, or private. For example, the user can "point and click" to user interface elements such as buttons, pull down menus, and scroll bars. The user requests can be transmitted to a Web application that formats them to produce a query that can be used to gather information from the SNP Data Mining database and from public or privately connected SNP databases.

Different database systems can use different identifiers to describe the same collection of nucleic acids onto which SNPs have been annotated. In this context, annotation of a SNP refers to its genomic location within a nucleic acid. Through the Web browser of the SNP Data Mining database, the user can construct search requests for retrieving intragenic SNPs in other SNP databases for annotating relevant valid SNPs. The genomic DNA is the most valuable source sequence to search for intragenic SNPs using the present invention; nonetheless, cDNA can be used as well. For example, BLAST can be used for annotating intragenic SNPs while data mining SNP databases for selecting relevant validated SNPs, although any appropriate sequence software or algorithms can be used in the context of the computer-based methods of the present invention. The user can select a candidate nucleic acid sequence onto which the user can annotate relevant valid SNPs.

In one embodiment, the operations that can be performed through the Web browser include, but are not limited to, downloading SNP databases, generating SNP output files by comparing nucleic acid subsequences obtained from a candidate nucleic acid sequence against the SNP databases using BLAST, storing the SNP output files, analyzing the SNP output files based on stored criteria, and annotating the validated SNPs. The algorithm can automatically discard SNPs that are annotated in repeat regions from further analysis. In addition, the nucleic acid positions for the validated SNPs can be recalculated in the candidate nucleic acid.

In a specific embodiment, the criteria for validating the BLAST hits can be one of percentage identity, BLAST hit length in percentage or BLAST hit length longer than about 250 bp, and location in non-repetitive DNA. Choosing stringent criteria, the user can validate relevant SNPs by selecting the hits that comply with a minimum of about 98% identity, the BLAST hit length covering at least about 98% of the length of the SNP entry in the database or is longer than 250 bp, and location in non-repetitive DNA.

One embodiment of the present invention comprises displaying the relevant valid SNPs on a computer readable medium.

An exemplary script used for the computer implemented method of annotating intragenic SNPs using the present invention can be the following, whose purpose is to convert a FASTA file (with, for example, the gDNA sequence) into an EMBL file with regions, repeats, and SNPs annotated. The procedures described below generate so-called EMBL features that, together with the nucleotide sequence of the FASTA file, constitute an EMBL file containing all necessary information on that gene. From this EMBL file, a summary file can be created that comprises the queried gene in a table format and the nucleotide position of the identified SNPs in the gene, whether or not the SNP is located in a repeat (Y/N), the intragenic context of the SNP, and the SNP-ID(s). For example:

| 576 | N | promoter | rs2020917 | |
|------|---|----------|-----------|---|
| 1026 | N | exon__utr5 | SNP000063116 | rs1805052 |
| 1801 | N | intron | SNP000555309 | rs737866 |
| 1813 | N | intron | SNP000555308 | rs737865 |
| 1851 | N | intron | SNP000555307 | rs737864 |
| 2788 | Y | intron | rs933269 | |
| 2865 | N | intron | rs933270 | |
| 3099 | N | intron | rs933271 | |
| 3360 | N | intron | rs1544325 | |
| 3587 | Y | intron | SNP000386819 | |
| 3781 | Y | intron | SNP000108169 | |
| 3782 | Y | intron | SNP000193205 | SNP000221543 |

The FASTA file with exons in uppercase (as available in the Human Genome Working Draft at UCSC) and a file containing the CDS region on the cDNA, for example gene_overview.txt, are used as input files. The summary EMBL file is created through the subsequent application of (1) creating features for the EMBL file (CDS, repeats, exon, intron, promoter, 5' and 3'UTR, SNPs), and (2) parsing the EMBL file to create the summary file.

In creating the features for EMBL file, several input files are used: the original FASTA file (with exons in uppercase), the gene_overview file, and the structure of gene_overview file. For example:
CYP2A6:
  NM_000762
  cytochrome P450, subfamily ILIA
  chr19:48317128-48325023
  CDS: 10.1494
CYP2C9:
  NM_000771
  cytochrome P450, subfamily IIC, polypeptide 9
  chr10:102259238-102310918
  CDS: 1 . . . 1473

The gene_overview file contains the CDS range on the cDNA sequence, which will be recalculated to the gDNA sequence.

The procedure for outputting the EMBL features includes: (1) creating repeat features, (2) creating exon features, (3) creating promoter features, (4) creating CDS, 5'UTR, and 3'UTR features, (5) creating intron features, and (6) creating SNP features.

To create repeat features, for example, the gDNA FASTA file is blasted against repbase (parameters: -p blastn -d repbase -e 1e-12). The FASTA file is parsed to read sequence into array @sequence and further:
  1) Read positions from lines beginning with "Query:",
  2) sort positions: $start_position and $end_position,
  3) replace elements of @sequence for these positions to "N":
  $sequence{$position}="N", 4) go through sequence with counter and detect when a "N" appears,
5) put counter in variable $repeat_start,
6) continue parsing sequence and detect when a non-"N" appears,
7) put counter in variable $repeat_stop, and
8) write to output:
FT repeat $repeat_start . . . $repeat_stop
FT /label="repeat"

Reading the sequence from the original gDNA FASTA file into an array @sequence using, for example, the following steps create exon features:
1) go through sequence with counter and detect when an uppercase nucleotide appears,
2) put counter in variable . . . $exon_start,
3) continue parsing sequence and detect when a lowercase nucleotide appears,
4) put counter in variable . . . $exon_stop,
5) write to output:
FT exon $exon_start . . . $exon_stop
FT /label="exon . . . $number"
6) remember exon numbers, positions and lengths (array @gDNA_exons:
"gdna_exon_number=$exon_number;
gdna_exon_start=$exon_start;
gdna_exon_stop=$exon_stop;
gdna_exon_length=$exon_length"),
7) find position of exons on the cDNA (necessary to calculate CDS and UTR's):
for each exon in @gDNA_exons:
if first exon: $cdna_start=1, else
$cdna_start=$cdna_stop+1
$cdna_stop=$cdna_start+$exon_$length
put this info in an array (@cDNA_exons, cfr @gDNA_exons),
8) write cDNA sequence to new cDNA FASTA file (necessary for BLAST of cDNA against SNP databases).

The following steps, for example, create the promoter feature:
1) input: @gDNA_exons,
2) promoter_start=1,
3) promoter_end=start first exon−1,
4) write to output:
FT promoter $promoter_start . . . $promoter_stop
FT /label="promoter"

The following steps can be used to create CDS, 5'UTR and 3'UTR features:
1) @gDNA_exons,
2) @cDNA_exons,
3) CDS info from file gene_overview.txt: CDS_start and CDS_stop,
4) find start of 5'UTR and end of 3'UTR,
5) start of 5'UTR=$exon_start of first exon in array @gDNA_exons,
6) end of 3'UTR=$exon_stop of last exon in array @gDNA_exons,
7) find CDS, end of 5'UTR and start of 3'UTR,
8) go through array @cDNA_exons,
9) if CDS_start is between $cdna_exon_start and $cdna_exon_stop:
calculate the length of the exon up to the CDS: $length=$cds_start−$cdna_exon_start,
take number of exon and search for that exon in array @gDNA_exons,
recalculate $cds_start to gDNA level: $cds_start=$gdna_exon_start+$length, and
end of 5'UTR=start of CDS−1
10) if CDS_stop is between $cdna_exon_start and $cdna_exon_stop,
calculate the length of the exon up to the CDS: $length=$cds_start−$cdna_exon_start,
take number of exon and search for that exon in array @gDNA_exons,
recalculate $cds_stop to gDNA level: $cds_stop=$gdna_exon_start+$length, and
start of 3'UTR=end of CDS+1
11) write to output:
FT CDS $CDS_start . . . $CDS_stop
FT /label="coding sequence"
FT 5'UTR $utr5_start . . . $utr5_stop
FT /label="5"UTR"
FT 3'UTR $utr3_start . . . $utr3_stop
FT /label="3"UTR"

The following steps can be used to create intron features:
1) @gDNA_exons,
2) number of introns=number of exons−1,
3) end of first exon+1=start of first intron,
4) start of second exon−1=stop of first intron, to be repeated for each following input, and
5) write to output:
FT intron $intron_start . . . $intron_stop
FT /label="intron $number"

To create the SNP features, input sequences are chopped sequences (parameters: $chunksize and $overlap) and the following steps can be used:
1) Input file: FASTA gDNA and cDNA sequences,
2) put sequence in array @seq,
3) write @seq to outputfile as in Example 2a,
4) output: gDNA FASTA file and cDNA FASTA file, and
5) BLAST the chopped gDNA and cDNA against dbSNP and HGBASE using, for example, the parameters:
-p blastn,
-i chopped FASTA file,
-d SNP database,
-e 1e-12,
-v 2000,
-b 2000, and
-F F,
6) output: BLAST file (see Example 2b),
7) select relevant BLAST hits, and
8) parse the BLAST output file (see Example 2c) and read info into array @snp_unsorted.

Each element of @snp_unsorted can contain the following information:
a) Start and stop position of the query sequence (DNA sequence),
b) start and stop position of the subject sequence (SNP sequence),
c) subject description,
d) % identity,
e) expectation value (e-value),
f) subject length,
g) identity ration,
h) query header (to extract segment),
i) SNP ID (for HGBASE: SNPxxx, for dbSNP: rsxxx),
j) allele position,
k) minimum length=(98/100), and
l) subject length.
9) select those entries from @snp unsorted that comply with the chosen criteria:
write relevant BLAST hits to a hashSNP (key of this hash=SNP_POSITION+SNP_ID;
value=SNP_POSITION+SNP_ID+SNP_DESCRIPTION), 10) discard all hits with a percentage identity <98%,
11) discard all hits where the allele position is not located in the subject sequence,
12) recalculate SNP positions to unchopped sequence (see Example 2d), count the number of gaps in the subject and query sequence:
    count every nucleotide in the subject sequence that is equal to "−" until the start position is equal to the allele position,
    for every nucleotide processed in the subject sequence, count every nucleotide in query sequence that is equal to "−",
13) if start position of subject<stop position of subject:
    SNP position=start position of query sequence
        −start position of subject sequence
        +allele position
        −amount of query gaps
        +amount of subject gaps
14) else:
    SNP position=start position of query sequence
        +start position of subject sequence
        −allele position
        −amount of query gaps
        +amount of subject gaps
15) if input sequence=cDNA: recalculate SNP position to gDNA:
    use arrays @gDNA_exons and @cDNA_exons from step "create exon features,"
    using @cDNA_exons: find out in which exon the SNP is located on the cDNA,
    count the number of nucleotides from the start of that exon until the SNP position,
    get the start position of that exon on the gDNA level, and add the two numbers above to get the SNP position on the gDNA,
16) if subject length>250 nucleotides: retain SNP,
17) else: if hit length>98% of subject length: retain SNP, and
18) for each entry inSNP: write output:
FT variation $position . . . $position
FT /label="dbSNP rsxxx"
Parsing the EMBL file to create the summary file requires an input file, for example, the EMBL file with SNP, exons, CDS, 5'UTR, 3'UTR, promoter, introns and repeats annotated, and an output file, for example, the described SNP summary file. The following steps can be implemented:
1) Read through EMBL file and put data in arrays:
2) if line starts with "FT promoter": put the start and stop positions in the array @promoter,
3) same for exon_cds, exon_utr5, exon_utr3, intron, and repeat,
4) for SNPs: will be added to a hash with the position as the key if line starts with "FT variation,"
5) remember position,
6) check next line ("label") for the SNP ID,
7) add the SNP ID to the hash: $SNP {$position}.=$SNP_ID CAUTION: do not use $SNP{$position}=$SNP_ID, as it is possible that more than one SNP is annotated on the same position
8) add the SNP position to the array @SNP_positions,
9) create a sorted list of SNP positions based on the array @SNP positions: @SNP_positions_sorted,
10) go through array @SNP_positions_sorted and write data to output (fields in summary: position, repeat[Y|N], region, SNP IDs):
11) for each line in @SNP_positions_sorted:
    set default region to "−",
    set default repeat to "N"
12) for each line in @promoter (this array consists of only one entry):
13) if SNP position lies between start and stop of the promoter, set $region to "promoter,"
14) same for exon_utr5, exon_cds, intron and exon_utr3,
15) for each line in @repeats:
16) if SNP position lies between start and stop of repeat, set $repeat to "Y," and
17) write to output:
$SNP_position_sorted $repeat $region $SNP{$SNP position_sorted}

In another embodiment, the SNP Data Mining database makes available the high quality SNPs selected based on methodology of the present invention. The user can "point and click" to user interface elements and transmit a request to a Web application that formats them to produce a query that can be used to gather information from the SNP Data Mining database, based, for example, on sequence information data obtained by the user, and/or other phenotypic or genotypic information.

Specifically, the user can submit SNP data based on SNP information obtained by analyzing a patient's genetic makeup or parts of it. In this way, the user can use the SNP Data Mining database system of the present invention to determine an association between a SNP to a pathological condition and/or to a drug response based on that information by initiating the system to perform a comparison of the user's SNP genetic data with the SNP genetic data contained in the SNP Data Mining database.

By way of example, the system compares the SNP genetic information submitted by the user with SNP genetic data contained in the database and then provides the user with information of pathological association and/or drug response association based on the best match of the user SNP genetic information with the SNP Data Mining database's genetic information. In a specific embodiment of the present invention, but not by way of limitation, this information can be provided on a computer readable medium. In addition, the website can provide hypertext links to public databases such as GenBank and associated databases maintained by the National Center for Biotechnology Information (NCBI), part of the National Library of Medicine as well as, any links providing relevant information for gene expression analysis, genetic disorders, scientific literature, and the like.

The methods of the present invention also include methods for determining association between a SNP to a pathological condition and association between a SNP to a drug response.

In one embodiment, these methods can comprise generating subsequences of nucleic acids from a candidate nucleic acid sequence, comparing each subsequence against a SNP database to obtain relevant SNP output files, analyzing the SNP output file for relevant valid SNPs, and annotating the relevant valid SNPs.

In another embodiment, these methods can comprise downloading nucleic acid sequence data information from a SNP database, generating SNP output files by comparing nucleic acid subsequences obtained from a candidate nucleic acid sequence against a SNP database using BLAST, storing the output files and analyzing those for valid SNPs based on stored criteria, and annotating the relevant valid SNPs. In addition, the methods can comprise recalculating nucleic acid positions for the relevant valid SNPs in the candidate nucleic acid sequence.

Further, the present invention provides methods based on providing a SNP Data Mining database to determine an association between a SNP and pathological condition and/or a drug response. This method comprises the steps of receiving SNP data, for example, obtained from a patient, and comparing the received SNP genetic data with the SNP genetic data contained in the SNP Data Mining database.

By way of example, the received SNP genetic information is compared with SNP genetic data contained in the database and information of pathological association and/or drug response association. Next, the best match of the user SNP genetic information with the SNP Data Mining database's genetic information is then communicated to the submitting party.

EXAMPLES

Without further elaboration, it is believed that one skilled in the art, using the preceding description, can utilize the present invention to the fullest extent. The following examples are illustrative only, and not limiting of the remainder of the disclosure in any way whatsoever. One skilled in the art can adapt the following techniques for annotating SNPs onto candidate genes based on any appropriate database.

Example 1

Data Mining of SNP Databases for the Selection of Intragenic SNPs

The data mining methodology of the present invention was used to identify intragenic SNPs comprised in two publicly accessible databases, dbSNP and HGBASE. The present invention was used efficiently by applying the BLAST algorithm with appropriate threshold settings to these databases. The data mining methodology of the present invention revealed additional and high quality SNPs compared to the SNPs that are annotated by the respective database websites.

Databases

Figure 2:
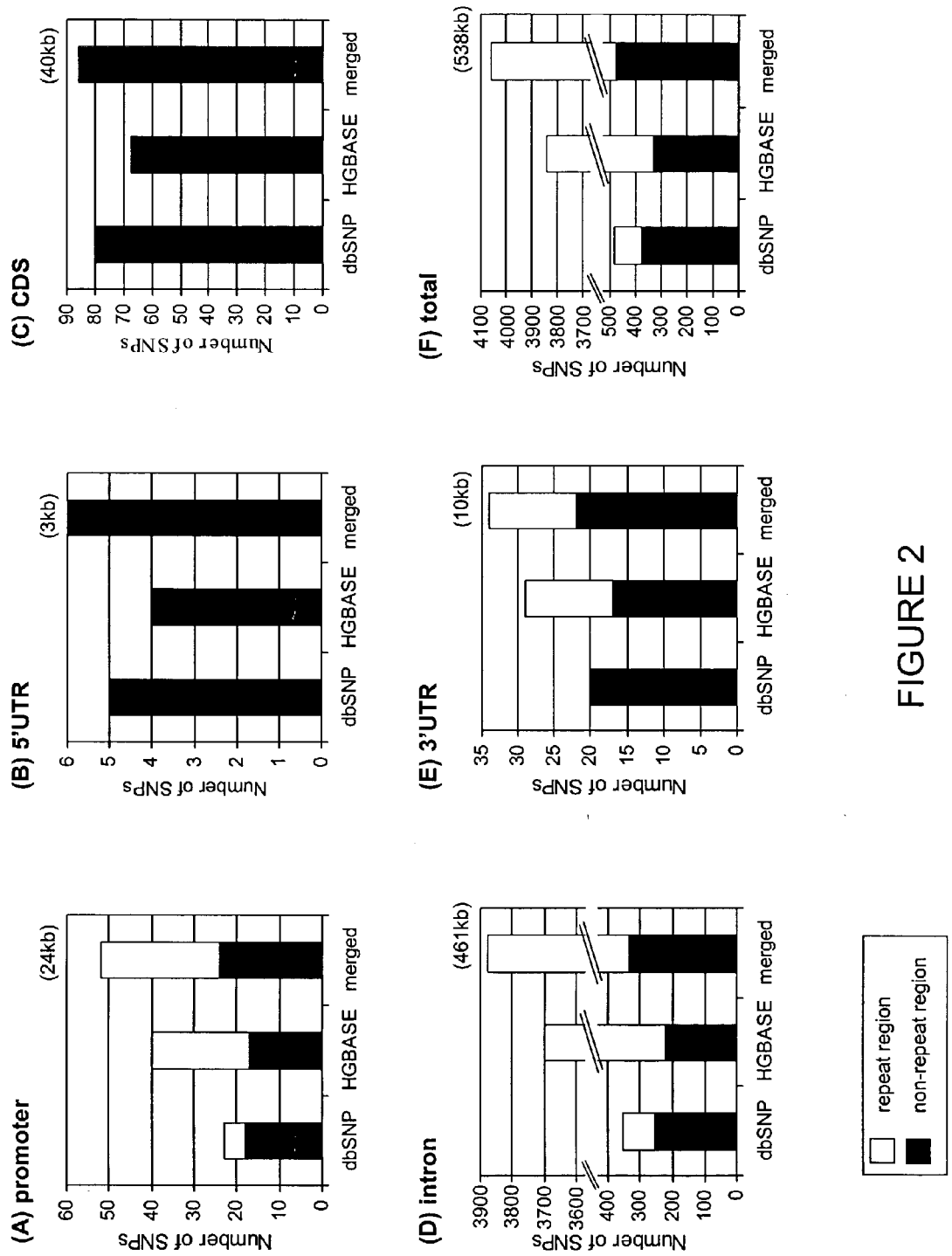
FIG. 2 provides the distribution of SNPs annotated to specific genes by the methods of the present invention stratified by intragenic region. Data are shown for SNPs obtained from dbSNP and HGBASE, and from a merged analysis. Each bar is divided into the share annotated in repeat regions (upper, white) and the share annotated in non-repeat regions (lower, black).
Figure 3:
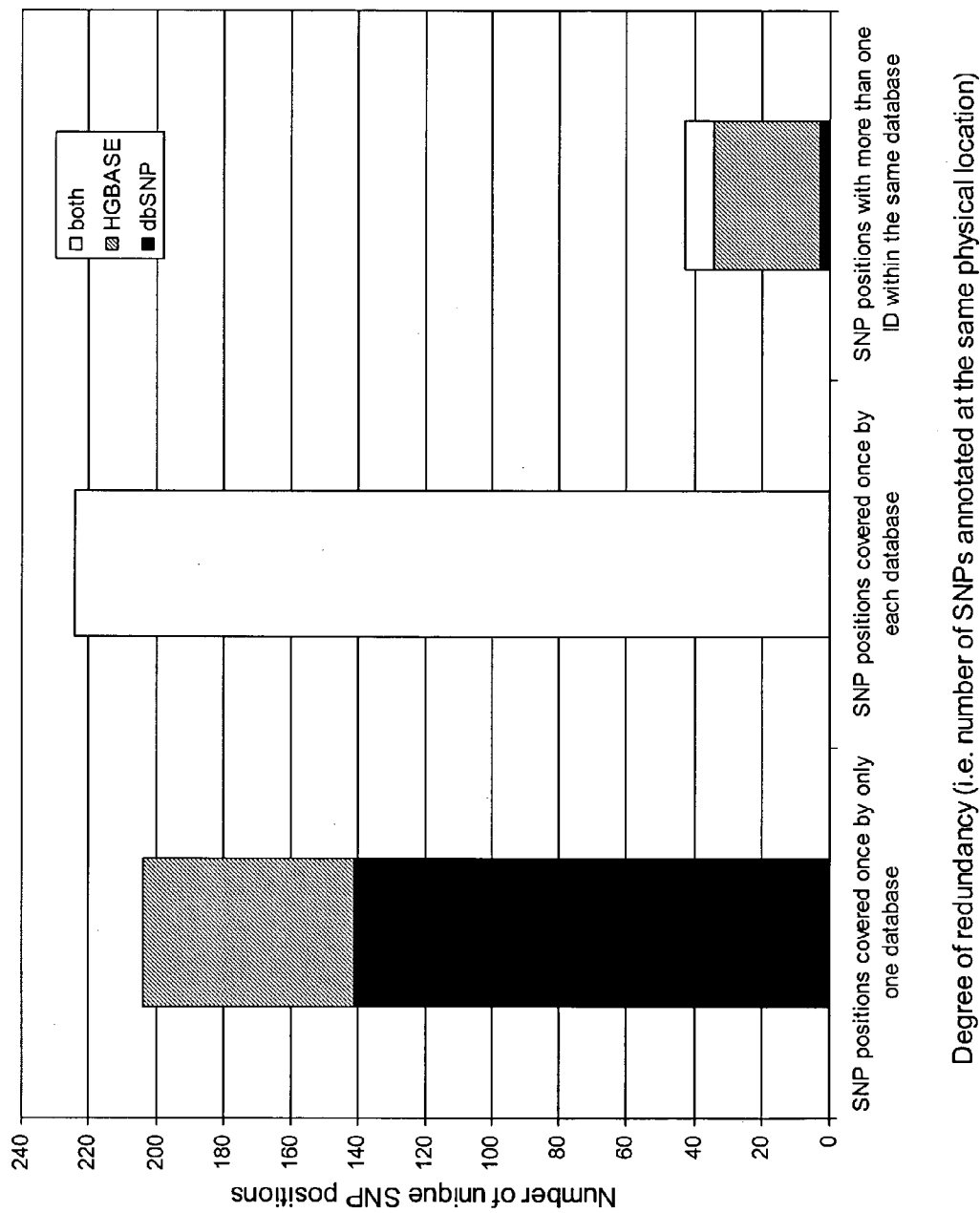
FIG. 3 provides the number of physical SNP positions, stratified by degree of redundancy of the annotation. Redundancy is defined as the number of independent SNP IDs annotated onto a unique physical location. The figure also shows the share of SNP positions with only SNP IDs from dbSNP (black), the share with only SNP IDs from HGBASE (shaded), and the share with SNP IDs from both databases (white).

The data for this analysis comprised the DNA sequences of 24 genes available in the public domain. FIGS. 2 and 3 provide detailed information on these genes, of which FIG. 3 specifically provides the total length of each genomic region and the length of the non-repetitive DNA in this region for all 24 genes analyzed in this study.

Genomic and cDNA sequences were obtained from the Dec. 12, 2000 freeze of the Human Genome Project Working Draft at UCSC. Each genomic sequence comprised a 1 kb region upstream of the 5' end of the first exon expected to include (at least part of) the promoter, until and including the 3' untranslated region (3'UTR). The boundaries of the intragenic regions (5'UTR, coding sequence, introns, 3'UTR) were derived from the same website.

Blastable SNP databases were downloaded from public ftp-sites and installed locally. These included the Aug. 6, 2001 download of the non-redundant reference SNP data of dbSNP, version 10.0 of HGBASE, and version 6.6 of the repeat database REPBASE. See Jurka et al., 16 TRENDS GENET. 418-20 (2000).

Intragenic SNP Annotation Using BLAST Search

The data mining methodology of the present invention based on a BLAST search was applied to the genes' genomic and cDNA sequences against local copies of the chosen SNP databases. The data mining methodology of the present invention comprises four major steps that were applied for each of the 24 genes analyzed. FIG. 1 provides a schematic overview of the data mining methodology of the present invention utilizing the BLAST program.

First, the genomic and cDNA sequences were chopped into subsequences of 1500 bp, with an overlap of 250 bp between flanking subsequences. Second, these subsequences were blasted against local copies of the downloaded SNP databases, with a maximum number of description lines set at 2000 SNP hits per subsequence in the reported output file. The dbSNP and HGBASE databases were analyzed successively and independently.

Second, the relevant SNPs were selected from these BLAST output files. Accordingly, a BLAST hit was considered a valid SNP if it complied with the following criteria: (1) the actual SNP was located within the boundaries of the BLAST hit, (2) its expectation value was below $10^{-12}$, (3) there was a minimum of 98% identity between SNP hit and query sequence, and (4) the hit length exceeded 250 bp, or alternatively equaled a minimum of 98% of the context length of that SNP in the SNP database (defined as relative hit length).

The threshold of 98% on the relative hit length was predefined to ensure that the whole database SNP entry would match the query sequence. The initial chopping procedure, with overlapping fragment size set at 250 bp, necessitated dropping this requirement in case of BLAST hit lengths longer than 250 bp. In such case, the limited size of the chopped subsequence that was used as query sequence in the BLAST searches can result in a BLAST hit length that is much smaller than the context sequence in the database SNP entry.

Third, the outcomes of the individual BLAST analysis of each of the chopped subsequences were integrated into the original cDNA or genomic gene sequence. Subsequently, the SNPs in the cDNA sequence were further integrated with the results of the genomic sequence, resulting in one summary table with all intragenic SNPs for each individual gene.

Finally, a search for all repeat regions was performed by blasting the genomic sequences against the REPBASE database, with an upper limit on the expectation value of $10^{-3}$. Only SNPs located in non-repeat regions were finally retained by the data mining methodology of the present invention. See FIG. 3.

Genetic Context and Redundancy of the SNPs

Following annotation by the data mining methodology of the present invention, the genetic context and redundancy of these SNPs were assessed. As the nucleotide positions were calculated by the present invention, different SNP IDs that referred to the same physical SNP were matched, and the genomic region (i.e., repeat, promoter, coding sequence) was defined.

Annotation Quality at dbSNP and HGBASE Websites

The dbSNP and HGBASE websites were searched by gene name to yield a list of SNPs annotated to that gene by these websites. All 24 genes were searched on the websites on the same day as when the SNP databases were downloaded (Aug. 6, 2001). Two analyses were performed on these SNP entries. First, the list of SNPs annotated by the websites was compared to the list of SNPs annotated by the data mining methodology of the present invention. Next, the flanking regions of all retrieved SNPs annotated by the websites were extracted from the downloaded databases and aligned with the genomic and the cDNA subsequences of the corresponding gene using the BL2SEQ algorithm (part of the BLAST package).

The first part of the analysis verified the sequence context and redundancy of the high quality SNPs that were selected based on the data mining methodology of the present invention. FIG. 2 provides the number of SNPs identified in the set of 24 genes stratified by intragenic region (promoter, 5'UTR, coding sequence, intron, and 3'UTR). Individual data for each of the 24 genes is presented in FIGS. 7 and 8. The large majority (91%) of the initially selected SNPs from HGBASE were annotated on (mostly intronic) repeat regions. For dbSNP, this fraction was only 22 of the selected SNPs. The algorithm of the present invention automatically discarded SNPs that were annotated in repeat regions for all further analyses.

Overall, the number and distribution of intragenic SNPs in non-repeat regions was similar in dbSNP and HGBASE, regardless of the intragenic region. A total of 377 and 327 SNPs were identified in non-repeat regions for dbSNP and HGBASE, respectively. A merger of identified SNPs from both databases resulted in a total of 471 unique SNPs residing in non-repeat regions. Of those, 86 SNPs (18%) were located in the coding sequence of the genes. Forty-eight of these SNPs (56%) in the coding sequence caused non-synonymous changes (n=46) or stop codons (n=2) in the amino acid sequence of the encoded protein. Based on the combined analysis of dbSNP and HGBASE, overall SNP densities of 1 SNP/901 bp in the promoter, 1 SNP/457 bp in the 5'UTR, 1 SNP/460 bp in the coding sequence, 1 SNP/1078 bp in the introns, and 1 SNP/404 bp in the 3'UTR were found in the non-repeat regions.

FIG. 3 presents the degree of redundancy according to database source. Redundancy is defined as the number of SNP IDs annotated at the same physical location. The 377 unique SNP positions identified by dbSNP were covered by 387 different SNP IDs. For HGBASE, 327 unique SNP positions were covered by 437 SNP IDs. Despite a large overlap of SNPs present in both dbSNP and HGBASE, a non-negligible number of SNPs was found in only one of the two. More specifically, 204 SNPs (43%) were covered once by only one of the databases, 224 SNPs (48%) were covered once by both databases, and 43 SNPs (9%) had redundant annotations within at least one of the same databases.

Focusing on the intragenic regions comprised in the cDNA (5' UTR, CDS and 3' UTR) assessed the added value of the genomic and cDNA sequences. This value determined how many SNPs of the 105 (5+80+20) dbSNPs and how many SNPs of the 88 (4+67+17) HGBASE SNPs could be picked up using either the genomic or cDNA sequence only.

Using the data mining methodology of the present invention on the genomic DNA alone yielded 90% (95 out of 105) of the dbSNPs and 97% (85 out of 88) of the HGBASE SNPs that were identified using both the genomic and cDNA sequences. When only the cDNA sequences were used, of all SNPs identified in this study 65% (68 out of 105) of the dbSNPs and 84% (74 out of 88) of the HGBASE SNPs were found. Therefore, the genomic DNA can be a preferable source sequence to search for intragenic SNPs in dbSNP and HGBASE using the data mining methodology of the present invention.

To assess the validity of the SNPs detected by the data mining methodology of the present invention, the results for some genes were compared with wet laboratory SNP screening studies reported in literature. Cauchi et al., 22 CARCINO-GENESIS 1819-24 (2001), performed a polymorphism screening of the AHR gene in 30 individuals, with a focus on the promoter and exons. Cauchi identified 3 SNPs, one of which was also annotated by the present invention. Furthermore, the present invention's data mining methodology identified 3 additional SNPs in these intragenic regions. A review by Raunio et al., reported on the polymorphisms found in the CYP2A6 gene and refers to the CYP2A6-specific website for a full list of polymorphisms. Raunio et al., 52 Br. J. CLIN. PHARMACOL. 357-63 (2001). The website (updated Jun. 11, 2001) listed 6 SNPs in the CYP2A6 gene, one of which was also annotated by the methodology of the present invention. The present invention annotated 8 SNPs that the website did not list. Two independent studies document 3 polymorphic sites in the coding region of the MTHFR gene. van der Put et al., 62 AM. J. HUM. GENET. 1044-51 (1998) and Weisberg et al., 64 MOL. GENET. METAB. 169-72 (1998). The present invention's data mining methodology also found two of these polymorphisms. Five polymorphisms annotated by the present invention in the coding region were not reported in these articles. Importantly, none of the SNPs reported in these publications but not detected by the methods of the present invention were present in the dbSNP or HGBASE databases.

Evaluating the Quality of the Annotation Presented by SNP Databases

Figure 4:
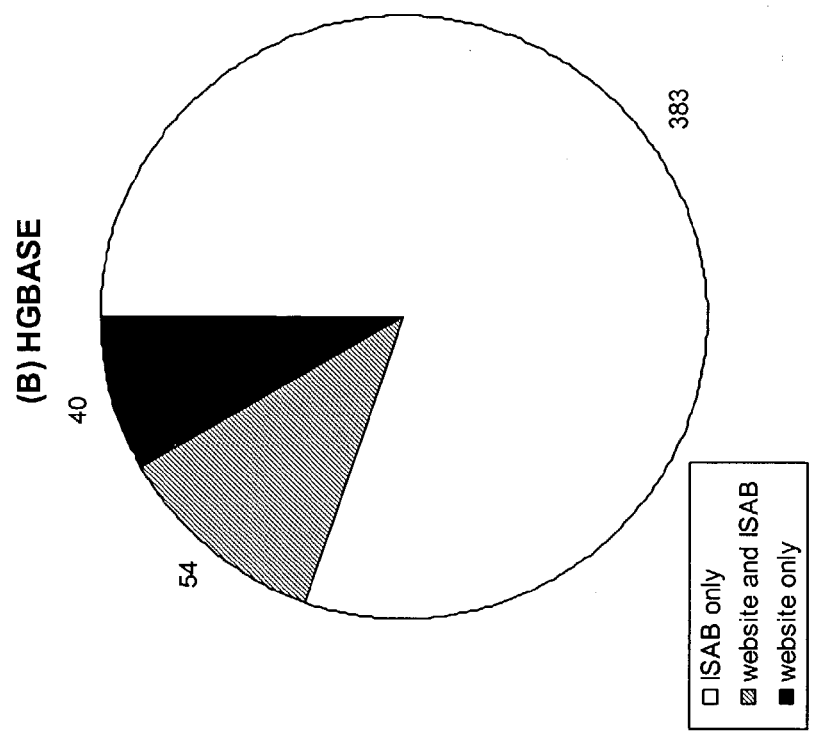
FIG. 4 shows the degree of redundancy according to database source. Redundancy is defined as the number of SNP IDs annotated at the same physical location. The 377 unique SNP positions identified by dbSNP were covered by 387 different SNP IDs. For HGBASE, 327 unique SNP positions were covered by 437 SNP IDs. Despite a large overlap of SNPs present in both dbSNP and HGBASE, a non-negligible number of SNPs was found in only one of them. More specifically, 204 SNPs (43%) were covered only once by one of the databases, 224 (48%) were covered once by both databases, and 43 SNPs (9%) had redundant annotations within at least one of the databases.
Figure 4:
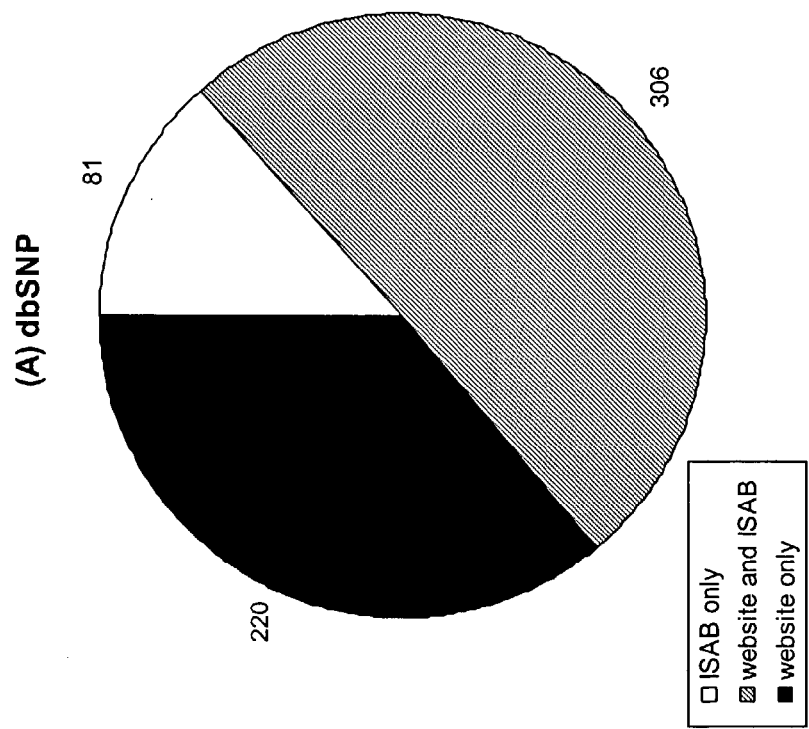
Figure 9:
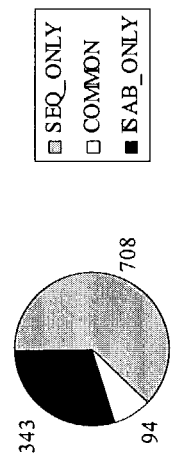
FIG. 9 provides a comparison of the results of different strategies to query the public SNP database HG(V)BASE. The queries involved either searching on the website by gene name ("NAME") or by gene sequence (cDNA) ("SEQ") or alternatively by using the strategy of the present invention (using chopped cDNA and gDNA sequences) ("ISAB").
Figure 9:
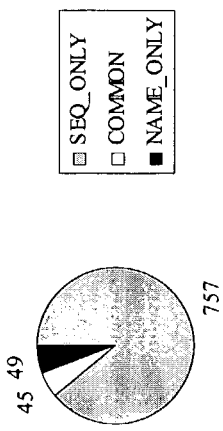

The second part of the analysis evaluated the quality of the annotation presented by the SNP databases. In this context, annotation of a SNP is defined as its genomic location within a gene. Therefore, the similarity between the annotation by the SNP database websites and the data mining methodology of the present invention was assessed. FIGS. 4 and 9 summarize the results of intragenic SNP selection performed by either searching the database websites by gene name or by applying the algorithm of the present invention.

The data in FIG. 4 indicates the number of SNP IDs rather than the number of unique SNP positions, because the degree of redundancy of the SNPs annotated only by the SNP databases websites could not be evaluated. Furthermore, the data based on the methodology of the present invention only includes SNPs that are not located in repeat regions, which could not be verified for the SNPs annotated by the SNP databases' websites only. Of all annotated SNPs, 50% (306 out of 607) of the dbSNPs and 11% (54 out of 477) of the HGBASE SNPs were in common between the two SNP databases websites annotation and the annotation made by the present invention.

Of all the intragenic SNPs in dbSNP, 220 SNPs (36%) were annotated exclusively by the dbSNP website. This result can be explained because either the present invention's criteria for valid SNPs were not fulfilled or there was a synchronization delay of the database version between the download (ftp) versus the website (see below). Blasting the dbSNP database, of all the 387 (306+81) hits annotated by the present invention, only 81 SNPs (21%) were not annotated by the dbSNP website. Blasting the HGBASE database, 40 SNPs annotated by its website did not comply with the criteria of the present invention. Of all the 437 (383+54) HGBASE hits annotated to the specified genes, the data mining methodology of the present invention exclusively annotated 383 SNPs (80%).

Remarkably, as low as 58% (306 out of (220+306)) and 57% (54 out of (40+54)) of all the intragenic SNPs annotated by the dbSNP and HGBASE websites, respectively, fulfilled the criteria of the present invention for a valid SNP. For each SNP annotated by the websites, the flanking regions were extracted from the downloaded databases and were aligned with the genomic and cDNA sequences of the corresponding genes using the BL2SEQ algorithm. Of the 526 SNPs annotated by the dbSNP website, 61 (i.e., more than 10 of the SNPs annotated by the dbSNP website) were not present in the database version that was downloaded by ftp on the same day (Aug. 6, 2001). It was discovered that later versions of the downloadable dbSNP database (i.e., from the version of Aug. 20, 2001, and onward) comprised all 61 SNPs, indicating that updates of the database used for the dbSNP website and the database available for download on the ftp website were not fully synchronized. The 465 SNPs that were present in the downloaded HGBASE database were blasted individually against the corresponding cDNA and genomic gene sequences (BL2SEQ algorithm). Of these SNPs, 69 did not produce a BL2SEQ hit with an expectation value lower than $10^{-12}$, and therefore were discarded for further annotation analysis. The BL2SEQ algorithm, however, produced significant hits for the other 396 SNPs. The downloaded HGBASE database comprised all 94 SNPs annotated by the website, but no significant BL2SEQ hit (i.e., expectation value below 10-12) was found for 29 HGBASE SNPs.

Figure 5:
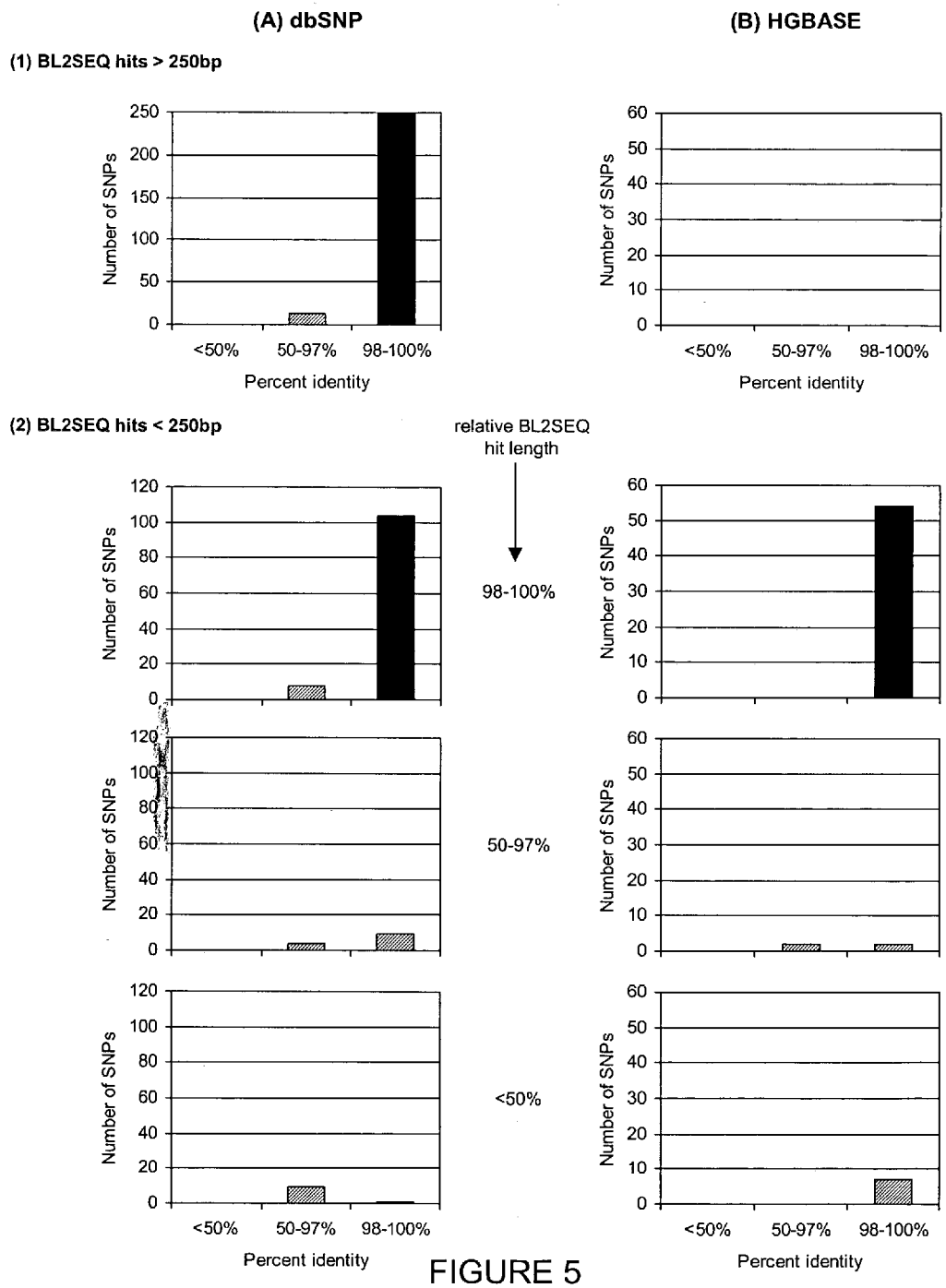
FIG. 5 provides the distribution of BL2SEQ hits according to hit length and percentage identity of SNPs annotated by the websites to map in one of the listed genes. For each SNP, the best BL2SEQ hit was selected based on identity and length (in this order). Part 1 shows the number of hits that are longer than 250 nucleotides; hits shorter than 250 nucleotides are displayed in part 2, stratified by relative BL2SEQ hit length (defined as the relative length of the BL2SEQ hit to the length of the SNP database entry). Bars in black represent BL2SEQ hits that comply with the criteria of the present invention to be selected for annotation.

For all SNPs for which a significant BL2SEQ hit was identified, the best hit was selected based on perentage identity and length (in that order). FIG. 5 presents the distribution of the SNP hits according to percentage identity and hit length. According to this stratification, only the SNPs that fulfilled the 98-100% criterion for percentage identity and that were longer than 250 basepairs (part 1) or showed a relative hit length greater than 98% (part 2) would have been selected by the data mining methodology of the present invention. Relative hit length was defined as the ratio of BL2SEQ hit length versus the context length of the SNP in the public database. Only a very limited number of the significant BL2SEQ hits have a low percentage identity, which results from the fact that the BLAST and BL2SEQ algorithms optimize primarily the percentage identity and only secondarily the hit length. Of note, the BL2SEQ search produced 7 SNPs that complied with the criteria of the present invention that were not found using the BLAST algorithm.

Example 2

Description of the Scripts Used for Embodiments of the Data Mining Methodology of the Present Invention The following example provides a description of the scripts that can be implemented as well as the output files generated from the methods of the present invention. This description is exemplary only and is not intended to be exhaustive. Those skilled in the art will be able to envision other scripts and output files for the annotation of SNPs that are within the scope and spirit of the present invention.

```
A. Chopped FATSA subsequence for RXRG gDNA
parameters:
$chunksize = 1500
$overlap = 250
Segments 1-3 have been assigned SEQ ID NOS 1-3, respectively
GAAAACTGTATGACAGACCCAAACATCAACGGGGTGCTTAGATTCTTTGATCTCGGGTCA

GTTCCACACAAGACAGGCTCTGTGTTAGTGAGGACCCAGTGGTGTTTTTGAACAGGCGGC

AGGATAACAATGGTATATAAAATAAATGCAGAGAAAGACCTCCACATCAAGCCAACCCCT

CCTCCCTACCTGTAAGTTTTCCACCTGAGTGAGCTCTGGCTCCAGCTGCACTTGTCAAAC

TCCCATTGTTAGAGCACAGATAAATGCTTCCGGCCACCCAAGCAGGAGAGGCCCACCTCA

ACTTAAGGGCTACTCTATTTTAGTTTTCCGTAGCTGGAGATTGAGTATCACGCTTTTCTA

ATCTTGTGCTTCTGAAAGGGCCCTGTTCTCTCTTGAACCCCACCCCCTCCTCCTTTCACA

GATCAAATACCAAGTACATTGGACAGATAGAAGTTCGAATGAGAAAATGCATTTTAATAA

AATCCCATTGATTTTTGTGGATGTAAGTCAAGGAACAGGCACCTAAAGAGTCTTCCATCC

CCTGCCGTCTCCCGCCTCTCTCCTGACCTACACCGGGCGGTCATACATCGATTGGCTTCC

TAGATAATAGATCGTGCCACCCGGTAGGGACCTCTGGGGACGCGCCGGGAGCTGGAAGAG

TCGCACGCAGCAGCCCAACCCTGAGTTAATCAAACTAGCAACAGGATCTCAAGCAGCAGC

GACGGCGGTGGCAAGAGTAGCGGTGACGGCGGCGGCGGCGGCGGCAGCATTATGCGT

GATTACTGACAGGCACCAGCTGCTGCCGCCACAGCCGTCTCAAACGCACTATGTGGACTC

TCCGATCTAGAGGCAGATTCCTGACTAATCCCAGAGGGCTGGCCCAGCCTGTGCTCCCCG

GGCTGCTAGGAAGCGATGACCACTCTTGTTAGCCCAAGTTGAAGAAAGCCGGGCTGTGCC

TGGGAGCCGAGAGAGGCGGTAATATTTAGAAGCTGCACAGGAGAGGAACATGAACTGACG

AGTAAACATGTATGGAAATTATTCTCACTTCATGAAGTTTCCCGCAGGCTATGGAGGTAA

GTATCTCCCTTGGGCTTCACTGCGTGGACCTGTATGAGAGACTGAGAAGAAATTGGGAAA

TACGAATGACTGGATTAGTATTGAATTAAAAGGAGAACATATATGTTTATATGCATATAT

AGTGTGTATATAGCGTTTCAGCGTGTGTGTGCACGCGTGCATGAGAGAGGAGAGGAGGAA

AGAATGGTCTGTAGGTGAGGATACGTTTGCATATCAGAATGAGGATACGGGGATATTCTA

AGGAGAGAGTAPACCAACATGCTTGAGAATGTGTCTGAGACAAAGATAGAATAAGAGCAT

TGTTATAACCCAGTGTGTTTGTGCGGGTGTGAAAAGTGGAAGAGTTAACGGGGAATTACT

ATGATGTTCCTATTAGCCAACTTGTAATGAGAAAAAATGTGATTAAAAAGGTTTTGCCTA
```

>[segment 2: 1251 . . . 2750] RXRG_gDNA
AGAGGAGGAAAGAATGGTCTGTAGGTGAGGATACGTTTGCATATCAGAATGAGGATACGG

GGATATTCTAAGGAGAGAGTAAACCAACATGCTTGAGAATGTGTCTGAGACAAAGATAGA

ATAAGAGCATTGTTATAACCCAGTGTGTTTGTGCGGGTGTGAAAAGTGGAAGAGTTAACG

GGGAATTACTATGATGTTCCTATTAGCCAACTTGTAATGAGAAAAAATGTGATTAAAAAG

GTTTTGCCTATCTTGAGGGTTCCTGGGATACTTTGTAACAAGGGCATGATTGTTTTACTC

AAAAGCAGATTTCCCTTTAATTGGATTTTAAAAAGAAAACATAGTGCTTTAATTTGCTA

CTGTGTTTTCCTTCCCCTGTTTTCTTTCCTTTGATTTGCTAATAGCCTCTTCTCTCCTCC

CCTGCTGCTGCCCCCAATTCTACTGCAAGAGTTGCTGCAATCACTTCCACTCTGGGGGTA

GAGATCTGGGGATGGGGGGTTGGGGCTCTTAGAGAATTGGCAAACTGAAGATTCAAGTCA

CCGTGCCAGGCAGGGCAGCCCAGTCACACTTCACAGAAGCTTCCGGAGACTAGGTCCTCA

GGCTGCCTTAACGCCCAAGCACATCTGTCCCAAGGATCCCTTGATTTAGTGACAGAAACA

GTACAGCCGCCCAGCTCTGAGTAAATGGAAGCAACAGCTGACCAACTGGCCTGTCGCTTG

TCAGTTGGAGGCATGCAGCTTATGTTGCTGGGAGCCAAAGAAAGATTCTGGCAGGCAAGA

CAGCAGAAATTCTTATAAGGTTTTGAAAATTGAAAAGTCCCTGCTCTCCAGACTTCCTCC

GTGGACCAATTCATCTGAAGGCTTGGGACTAAAGCTTGCCTAACTTGGCTGGGCAGAACC

CCCTGGGAGGCATGGTGACACACTGCAAGGTAGAAGTGATCTCTGTCACCAGGAGGTGTT

AGACCTGGGAGTTTGCACATTCATTCAGGGTAGTTTTTATGAGGCAGGCATGGTGTTGGG

CACTGGGAATACAAATATGAATGAGACACAGTCTCTGCCCTTTGGGACTGGGGCAGGCTT

GTTACACAGGCACATTATAATACTGCATGATGTGTGTAATAGCAAACGTAGGTTGTACTT

GGACTTGGGGTGAGGGCCATGGAAATGTTCCCGAGGTGATGTTCAAGTTCTTTGGGCCAG

TCTGATGACAGAGTGAGAGCGGTGGCCAATGCTGTGACCTGGGCATTTGATCTCTAGTCT

ATGGTTGGGCTCCAGATGTGAAAAGCCTCCTCAATTCCCACCTCAGTCCCATTCAGAGCT

GAGAATTGCTTTTTCCTTTACATCTTAGTTCATTTGTAAGAGGTGCATGCTCATTTTCAG

CCAGATTCGTGGGCCCCCCAAGGTCTGTGAGACTGTGGCTTCATTAATGCCAAAGAGACC

CTTGGAGACAGTTGGGGTGAATAAAAGGGTTGAAGCTAGAAGGATTTAGGGAGAGAACTA

>[segment 3: 250] . . . 4000]
TCTCTAGTCTATGGTTGG . . .

B. BLAST output file for RXRG gDNA
BLASTN 2.1.2 [Oct. 19, 2000]
Reference: Altschul, Stephen F., Thomas L. Madden, Alejandro
A. Schaffer,
Jinghui Zhang, Zheng Zhang, Webb Miller, and David J. Lipman
(1997),
"Gapped BLAST and PSI-BLAST: a new generation of protein
database search programs", Nucleic Acids Res. 25:3389-3402.
Query = [segment 1: 1 . . . 1500]xabcc2 cDNA
(1500 letters)
Database: dbsnp_rs-010809
1,439,194 sequences; 1,293,482,021 total letters
Searching . . . done
Score E
Sequences producing significant alignments: (bits) Value
gnl|dbSNP|rs927344_allelePos = 470
total len = 635
|taxid = 96061 . . . 349 1e-93
gnl|dbSNP|rs717620_allelePos = 207
total len = 611
|taxid = 9606|. . . 119 2e-24
>gnl|dbSNP|rs927344_allelePos = 470
total len = 635
|taxid = 9606|snpClass=1
Length = 635
Score = 349 bits (176), Expect = 1e-93

-continued

```
Identities = 177/178 (99%)
Strand = Plus/Plus
Query = SEQ ID NO: 4
Subject = SEQ ID NO: 5
                                        Query
        62   gaattcctcattcctggacagtccggaggcagacctgccactttgttttgagcaaactgt   121
             ||||||||||||||||||||||||||||||||||||||||||||||||||||||||||||
       387   gaattcctcattcctggacagtccggaggcagacctgccactttgttttgagcaaactgt   446
                                       Subject Query
       122   tctggtgtggattcccttgggctacctatggctcctggcccctggcagcttctccacgt    181
             |||||||||||||||||||||||| |||||||||||||||||||||||||||||||||||
       447   tctggtgtggattcccttgggctwcctatggctcctggcccctggcagcttctccacgt    506
                                       Subject Query
       182   gtataaatccaggaccaagagatcctctaccaccaaactctatcttgctaagcaggta    239
             ||||||||||||||||||||||||||||||||||||||||||||||||||||||||||
       507   gtataaatccaggaccaagagatcctctaccaccaaactctatcttgctaagcaggta    564
                                       Subject >gnl|dbSNP|rs717620_allelePos = 207
total len = 611
|taxid = 9606
|snpClass = 1
Length = 611
Score = 119 bits (60)
Expect = 2e-24
Identities = 61/62 (98%)
Strand = Plus/Minus
Query = SEQ ID NO: 6
Subject = SEQ ID NO: 7
                                        Query
         1   gtcttcgttccagacgcagtccaggaatcatgctggagaagttctgcaactctacttttt   60
             |||||| |||||||||||||||||||||||||||||||||||||||||||||||||||||
       212   gtcttygttccagacgcagtccaggaatcatgctggagaagttctgcaactctacttttt   153
                                       Subject
Query
        61   gg   62
             ||
       152   gg   151
Subject Database: dbsnp_rs-010809
Posted date: Aug. 9, 2001 9:26 AM
Number of letters in database: 536,874,458
Number of sequences in database: 559,641
Database: /db/idx/rls/blast2/dbsnp_rs.01
Posted date: Aug. 9, 2001 9:31 AM
Number of letters in database: 536,871,269
Number of sequences in database: 620,454
Database: /db/idx/rls/blast2/dbsnp_rs.02
Posted date: Aug. 9, 2001 9:34 AM
Number of letters in database: 219,736,294
Number of sequences in database: 259,099
Lambda     K        H
1.37       0.711    1.31
Gapped
Lambda     K        H
1.37       0.711    1.31
Matrix: blastn matrix:1-3
Gap Penalties: Existence: 5, Extension: 2
Number of Hits to DB: 1610508
Number of Sequences: 1439194
Number of extensions: 1610508
Number of successful extensions: 2
Number of sequences better than 1.0e-12: 2
length of query: 1500
length of database: 1,293,482,021
effective HSP length: 20
effective length of query: 1480
effective length of database: 1,264,698,141
effective search space: 1871753248680
effective search space used: 1871753248680
T: 0
A: 0
X1: 6 (11.9 bits)
X2:10 (19.8 bits)
```

```
S1:12 (24.3 bits)
S2:41 (81.8 bits)
BLASTN 2.1.2 [Oct. 19, 2000]
Reference: Altschul, Stephen F., Thomas L. Madden, Alejandro
A. Schaffer, Jinghui Zhang, Zheng Zhang, Webb Miller, and
David J. Lipman (1997), "Gapped BLAST and PSI-BLAST: a new
generation of protein database search programs", Nucleic Acids
Res. 25:3389-3402.
Query = [segment 2: 1251 . . . 2750]xabcc2 cDNA
(1500 letters)
Database: dbsnp_rs-010809
1,439,194 sequences; 1,293,482,021 total letters
Searching . . . done
***** No hits found ******
Database: dbsnp_rs-010809
Posted date: Aug. 9, 2001 9:26 AM
Number of letters in database: 536,874,458
Number of sequences in database: 559,641
Database: /db/idx/rls/blast2/dbsnp_rs.01
Posted date: Aug. 9, 2001 9:31 AM
Number of letters in database: 536,871,269
Number of sequences in database: 620,454
Database: /db/idx/rls/blast2/dbsnp_rs. 02
Posted date: Aug. 9, 2001 9:34 AM
Number of letters in database: 219,736,294
Number of sequences in database: 259,099
Lambda     K        H
1.37       0.711    1.31
Gapped
Lambda     K        H
1.37       0.711    1.31
Matrix: blastn matrix:1-3
Gap Penalties: Existence: 5, Extension: 2
Number of Hits to DB: 1519581
Number of Sequences: 1439194
Number of extensions: 1519581
Number of successful extensions: 0
Number of sequences better than 1.0e-12: 0
length of query: 1500
length of database: 1,293,482,021
effective HSP length: 20
effective length of query: 1480
effective length of database: 1,264,698,141
effective search space: 1871753248680
effective search space used: 1871753248680
T: 0
A: 0
X1: 6 (11.9 bits)
X2:10 (19.8 bits)
S1:12 (24.3 bits)
S2:41 (81.8 bits)
BLASTN 2.1.2 [Oct. 19, 2000]
Reference: Altschul, Stephen F., Thomas L. Madden, Alejandro
A. Schaffer, Jinghui Zhang, Zheng Zhang, Webb Miller, and
David J. Lipman (1997), "Gapped BLAST and PSI-BLAST: a new
generation of protein database search programs", Nucleic
Acids Res. 25:3389-3402.
Query = [segment 3: 2501 . . . 4000]xabcc2 cDNA
(1500 letters)
Database: dbsnp_rs-010809
1,439,194 sequences; 1,293,482,021 total letters
Searching . . . done
***** No hits found ******
Database: dbsnp_rs-010809
Posted date: Aug.9, 2001 9:26 AM
Number of letters in database: 536,874,458
Number of sequences in database: 559,641
Database: /db/idx/rls/blast2/dbsnp_rs. 01
Posted date: Aug. 9, 2001 9:31 AM
Number of letters in database: 536,871,269
Number of sequences in database: 620,454
Database: /db/idx/rls/blast2/dbsnp_rs .02
Posted date: Aug. 9, 2001 9:34 AM
Number of letters in database: 219,736,294
Number of sequences in database: 259,099
Lambda     K        H
1.37       0.711    1.31
Gapped
Lambda     K        H
1.37       0.711    1.31
Matrix: blastn matrix:1-3
```

-continued
```
Gap Penalties: Existence: 5, Extension: 2
Number of Hits to DB: 1289085
Number of Sequences: 1439194
Number of extensions: 1289085
Number of successful extensions: 0
Number of sequences better than 1.0e-12: 0
length of query: 1500
length of database: 1,293,482,021
effective HSP length: 20
effective length of query: 1480
effective length of database: 1,264,698,141
effective search space: 1871753248680
effective search space used: 1871753248680
T: 0
A: 0
X1: 6 (11.9 bits)
X2: 10 (19.8 bits)
S1: 12 (24.3 bits)
S2: 41 (81.8 bits)
BLASTN 2.1.2 [Oct. 19, 2000]
Reference: Altschul, Stephen F., Thomas L. Madden, Alejandro
A. Schaffer, Jinghui Zhang, Zheng Zhang, Webb Miller, and
David J. Lipman (1997), "Gapped BLAST and PSI-BLAST: a new
generation of protein database search programs", Nucleic Acids
Res. 25:3389-3402.
Query = [segment 4: 3360 . . . 4859]xabcc2 cDNA
(1500 letters)
Database: dbsnp_rs-010809
1,439,194 sequences; 1,293,482,021 total letters
Searching . . . done
Score E
Sequences producing significant alignments:
(bits) Value
gnl|dbSNP|rs1962102_allelePos = 105
total len = 791
|taxid = 9606 . . . 98 8e-18
>gnl|dbSNP|rs1962102_allelePos = 105
total len = 791
|taxid =
9606|snpClass = 1
Length = 791
Score = 97.6 bits (49), Expect = 8e-18
Identities = 58/61 (95%)
Strand=Plus/Plus
Query = SEQ ID NO: 8
Subject = SEQ ID NO: 9
```

```
                                Query
   814    caggaccccatcctgttctctggaagcctgaggatgaatctcgaccctttcaacaactac    873
          |||||||||||||||||||||  |||| ||||||||||||| |||||||||||||||||||
   711    caggaccccatcctgttctttggaaacctgaggatgaatcttgaccctttcaacaactac    770
                                Subject Query
  874  t 874
       |
  771  t 771
Subject
Database: dbsnp_rs-010809
Posted date: Aug. 9, 2001 9:26 AM
Number of letters in database: 536,874,458
Number of sequences in database: 559,641
Database: /db/idx/rls/blast2/dbsnp_rs.01
Posted date: Aug. 9, 2001 9:31 AM
Number of letters in database: 536,871,269
Number of sequences in database: 620,454
Database: /db/idx/rls/blast2/dbsnp_rs. 02
Posted date: Aug. 9, 2001 9:34 AM
Number of letters in database: 219,736,294
Number of sequences in database: 259,099
Lambda      K        H
1.37      0.711    1.31
Gapped
Lambda      K        H
1.37      0.711    1.31
Matrix: blastn matrix:1-3
Gap Penalties: Existence: 5, Extension: 2
Number of Hits to DB: 1510630
Number of Sequences: 1439194
Number of extensions: 1510630
Number of successful extensions: 2
```

```
-continued
Number of sequences better than 1.0e-12: 1
length of query: 1500
length of database: 1,293,482,021
effective HSP length: 20
effective length of query: 1480
effective length of database: 1,264,698,141
effective search space: 1871753248680
effective search space used: 1871753248680
T: 0
A: 0
X1: 6 (11.9 bits)
X2: 10 (19.8 bits)
S1: 12 (24.3 bits)
S2: 41 (81.8 bits)
C. Parsed RXRG BLAST output file
PROGRAM: BLASTN
DE_NAMES: dbsnp_rs-010809
DB_LENGTH: 1,439,194
Q_HEADER: [segment 1:1 . . . 1500]xx abcc2 cDNA
Q_LENGTH: 1500
Q_START: 62
Q_STOP: 239
Q_SEQ:
gaattcctcattcctggacagtccggaggcagacctgccactttgttttga
gcaaact<SNIP>gaccaagagatcctctaccaccaaactctatcttgctaagcaggta
(SEQ ID NOS 10-11, respectively, in order of appearance)
S_HEADER: gnl|dbSNP|rs927344_allelePos = 470 total len =
635 |taxid = 9606|snpClass = 1
S_DB: NULL
S_ACCNO: NULL
S_ORG: NULL
S_GN: NULL
S_MOL: NULL
S_DESC: gnl|dbSNP|rs927344_allelePos = 470 total len =
635 |taxid = 9606|snpClass = 1
S_LENGTH: 635
S_START: 387
S_STOP: 564
S_SEQ:
gaattcctcattcctggacagtccggaggcagacctgccactttgttttga
gcaaact<SNIP>gaccaagagatcctctaccaccaaactctatcttgctaagcaggta
(SEQ ID NOS 12-13, respectively, in order of appearance)
SCORE: 349
EXPECT: 1e-93
ID_RATIO: 177/178
ID_PERCENT: 99
POS_RATIO: NULL
POS_PERCENT: NULL
GAPS_RATIO: NULL
GAPS_PERCENT: NULL
STRAND: Plus/Plus
FRAME: NULL
//
PROGRAM: BLASTN
DE_NAMES: dbsnp_rs-010809
DB_LENGTH: 1,439,194
Q_HEADER: [segment 1:1 . . . 1500]xabcc2 cDNA
Q_LENGTH: 1500
Q_START: 1
Q_STOP: 62
Q_SEQ
gtcttcgttccagacgcagtccaggaatcatgctggagaagttctgcaactctacttttgg
(SEQ ID NO: 6)
S_HEADER: gnl|dbSNP|rs717620_allelePos = 207 total len =
611 |taxid = 9606|snpClass = 1
S_DB: NULL
S_ACCNO: NULL
S_ORG: NULL
S_GN: NULL
S_MOL: NULL
S_DESC: gnl|dbSNP|rs717620_allelePos = 207 total len =
611 |taxid = 9606]snpClass = 1
S_LENGTH: 611
S_START: 212
S_13 STOP: 151
S_SEQ:
gtcttygttccagacgcagtccaggaatcatgctggagaagttctgcaactctacttttgg
(SEQ ID NO: 7)
SCORE: 119
EXPECT: 2e-24
ID_RATIO: 61/62
```

```
ID_PERCENT: 98
POS_RATIO: NULL
POS_PERCENT: NULL
GAPS_RATIO: NULL
GAPS_PERCENT: NULL
STRAND: Plus/Minus
FRAME: NULL
//
PROGRAM: BLASTN
DB_NAMES: dbsnp_rs-010809
DB_LENGTH: 1,439,194
Q_HEADER: [segment 2: 1251 . . . 2750]xabcc2 cDNA
Q_LENGTH: 1500
Q_START: NULL
Q_STOP: NULL
Q_SEQ: NULL
S_HEADER: NULL
S_DB: NULL
S_ACCNO: NULL
S_ORG: NULL
S_GN: NULL
S_MOL: NULL
S_DESC: NULL
S_LENGTH: NULL
S_START: NULL
S_STOP: NULL
S_SEQ: NULL
SCORE: NULL
EXPECT: NULL
ID_RATIO: NULL
ID_PERCENT: NULL
POS_RATIO: NULL
POS_PERCENT: NULL
GAPS_RATIO: NULL
GAPS_PERCENT: NULL
STRAND: NULL
FRAME: NULL
//
PROGRAM: BLASTN
. . .
 D. Count Gaps
sub CountGaps {
 my ($s_seq
 ,$q_seq
 ,$s_start
 $allele_pos
 ,$snp_id) = @_;
 my($q_gap_before) = 0;
 my($s_gap_before) = 0;
    counting gaps in Subject sequence
  @s_seq = split(//,$s_seq);
  chomp(@s_seq);
  $tel = 0;
  $s_gap_before = 0;
  if (int($s_start)<int($s_stop) ){
   while ($s_start ne $allele_pos) {
      $nucl = $s_seq[$tel]
      if ($nucl eq "-") {
       $s_gap_before++;
      }else{
       $s_start++;
      }
      $tel++;
     }
     }else{
    while ($s_start ne $allele_pos) {
      $nucl = $s_seq[$tel]
      if ($nucl eq "-"){
       $s_gap_before++;
      }else{
       $s_start--;
      }
      $tel++;
     }
  }
    counting gaps in Query sequence
   @q_seq=split //,$q_seq;
   chomp(@q_seq);
   $q_index = 0;
  $q_gap_before = 0;
   while ($tel ne 0){
```

```
  $nucl = $q_seq[$q_index]
  if ($nucl eq "-") {
    $q_gap_before++;
  }
    $q_index++;
    $tel--;
  }
  return($q_gap_before, $s_gap_before);
}
```
E. SNP annotation for allele position output file
Alleleposition = 39, recalculated to gDNA should be: 888
Query = SEQ ID NO: 14
Subject = SEQ ID NO: 15
```
Query:   877     AC-GACTGAC-GAATGAC--ACT-GACT        899
                 || | |||||| || || |    |  |||
Subject:  51     ACTG-CTGACTGACTG-CTG--TG-ACT         29
Handling in CountGaps:
Counting gaps in Subject sequence
$allelepos             39|
$s_gap_before           0|             1
$s_start               51| 50 49 48 47    46 45 44 43 42 41 40 39
$tel                    0|  1  2  3  4     5  6  7  8  9 10 11 12 13
Counting gaps in Query sequence
$q_gap_before           0|       1                           2
$q_index                0|  1  2  3  4  5  6  7  8  9 10 11 12 13
$tel                   13| 12 11 10  9  8  7  6  5  4  3  2  1  0
$q_allele = 877+51-39-2+1 = 888 q.e.d.
```

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The disclosures of all references and publications cited above are expressly incorporated by reference in their entireties to the same extent as if each were incorporated by reference individually.

What is claimed:

1. A method for determining an association between a SNP and a population susceptible to a disease or a condition, said method comprising the steps of:
   receiving candidate nucleic acid sequences;
   generating subsequences of nucleic acids from said candidate nucleic acid sequences;
   comparing, by one or more processors, each of said subsequences against one or more SNP databases using a sequence comparison algorithm to obtain relevant SNP output files;
   analyzing said relevant SNP output files for relevant valid SNPs;
   discarding said relevant valid SNPs located within repeat regions of said candidate nucleic acid sequences to remove intragenic SNPs annotated in the SNP databases that are not relevant for genotyping;
   annotating said relevant valid SNPs onto the candidate nucleic acid sequences to assess the genetic content and redundancy of the relevant valid SNPs; and
   outputting said annotated relevant valid SNPs to a display, a memory or another computer on a network, wherein said outputted annotated relevant valid SNPs are SNPs associated with a population susceptible to said disease or condition.

2. The method of claim 1, wherein said discarding comprises comparing relevant valid SNPs against the REPBASE database.

3. The method of claim 2, wherein said comparing is performed using an expectation value limit of about $10^{-3}$.

4. The method of claim 1, further comprising recalculating nucleic acid positions for said relevant valid SNPs in said candidate nucleic acid sequence.

5. The method of claim 4, wherein said nucleic acid position is one or more selected from the group consisting of 5' untranslated region (5'UTR), promoter region, nucleic acid coding region, 3' untranslated region (3'UTR), and introns.

6. The method of claim 1, wherein said candidate nucleic acid sequence is genomic DNA (gDNA).

7. The method of claim 1, wherein said candidate nucleic acid sequence is complementary DNA (cDNA).

8. The method of claim 1, wherein said nucleic acid subsequences comprise a length between about 1000 base pairs (bp) and about 5000 bp.

9. The method of claim 8, wherein said nucleic acid subsequences have an overlap of nucleic acid sequence between flanking sequences within the range of about 100 bp to about 500 bp.

10. The method of claim 8, wherein said nucleic acid subsequences comprise a length of about 1500 bp.

11. The method of claim 10, wherein said nucleic acid subsequences have an overlap of 250 bp between flanking regions.

12. The method of claim 1, wherein said sequence comparison algorithm is a Basic Local Alignment Search Tool (BLAST).

13. The method of claim 12, wherein said comparing generates BLAST output files.

14. The method of claim 1, wherein said analyzing step comprises validating said relevant SNP output files.

15. The method of claim 14, wherein said validating comprises applying the following criteria:
   SNP location within boundaries of hit length; expectation value at least about $10^{-12}$ or below;
   minimum identity is about 98% or above between SNP hit and query sequence; and
   hit length is at least about 250 by or higher.

16. The method of claim 14, wherein said validating comprises applying the following criteria:
   SNP location within boundaries of hit length;
   expectation value at least about $10^{-12}$ or below;
   minimum identity is about 98% of the length of SNP entry in said one or more SNP databases;
   hit length equals at least about 98% of the length of SNP entry in said one or more SNP databases.

17. The method of claim 1, further comprising using a computer data based search engine to obtain additional information regarding said relevant valid SNPs.

18. The method of claim 17, wherein said additional information is selected from one or more of the group consisting of a compound, gene, cell, virus, sequence, and substance affecting said relevant valid SNP.

19. The method of claim 1, wherein said annotating comprises assigning said relevant valid SNP to a gene location.

20. The method of claim 1, wherein said annotating comprises assigning a gene name to said relevant valid SNPs.

21. A non-transitory computer readable medium bearing computer executable instructions for annotating SNPs onto candidate nucleic acid sequences comprising:
   instructions for receiving candidate nucleic acid sequences into the computing device;
   instructions for generating subsequences of nucleic acid from said candidate nucleic acid sequences;
   instructions for comparing each of said subsequences against one or more SNP databases using a sequence comparison algorithm to obtain relevant SNP output files;
   instructions for analyzing said relevant SNP output files for relevant valid SNPs;
   instructions for discarding said relevant valid SNPs located within repeat regions of said candidate nucleic acid sequence to remove intragenic SNPs annotated in the SNP databases that are not relevant for genotyping;
   instructions for annotating said relevant valid SNPs onto the candidate nucleic acid sequences to assess the genetic content and redundancy of the relevant valid SNPs; and
   instructions for outputting said annotated relevant valid SNPs to a display, a memory or another computer on a network,
   wherein said outputted annotated relevant valid SNPs are SNPs associated with a population susceptible to a disease or a condition.

22. The computer readable medium of claim 21, further comprising instructions for recalculating nucleic acid positions for said relevant valid SNPs in said candidate nucleic acid sequence.

23. The computer readable medium of claim 22, wherein said nucleic acid position is one or more selected from the group consisting of 5'UTR, promoter region, nucleic acid coding region, 3'UTR, and introns.

24. The computer readable medium of claim 21 further comprising an instruction for displaying said relevant valid SNPs on a computer readable medium.

25. The computer readable medium of claim 21, wherein said instructions for discarding comprise comparing relevant valid SNPs against the REPBASE database.

26. The computer readable medium of claim 25, wherein said instructions for comparing are performed using an expectation value limit of about $10^{-3}$.

27. The computer readable medium of claim 21, wherein said candidate nucleic acid sequence is gDNA.

28. The computer readable medium of claim 21, wherein said candidate nucleic acid sequence is cDNA.

29. The computer readable medium of claim 21, wherein said nucleic acid subsequences comprise a length between about 1000 bp and about 5000 bp.

30. The computer readable medium of claim 29, wherein said nucleic acid subsequences have an overlap of nucleic acid sequence between flanking sequences within the range of about 100 bp to about 500 bp.

31. The computer readable medium of claim 29, wherein said nucleic acid subsequences comprise a length of about 1500 bp.

32. The computer readable medium of claim 31, wherein said nucleic acid subsequences have an overlap of 250 by between flanking regions.

33. The computer readable medium of claim 21, wherein said sequence comparison algorithm is BLAST.

34. The computer readable medium of claim 33, wherein said instructions for comparing generate BLAST output files.

35. The computer readable medium of claim 21, wherein said instructions for analyzing comprise validating said relevant SNP output files.

36. The computer readable medium of claim 35, wherein said instructions for validating comprise applying the following criteria:
SNP location within boundaries of hit length;
expectation value at least about $10^{-12}$ or below;
minimum identity is about 98% or above between SNP hit and query sequence; and
hit length is at least about 250 by or higher.

37. The computer readable medium of claim 35, wherein said instructions for validating comprise applying the following criteria:
SNP location within boundaries of hit length;
expectation value at least about $10^{-12}$ or below;
minimum identity is about 98% or above between SNP hit and query sequence; and
hit length equals at least about 98% of the length of SNP entry in said one or more SNP databases.

38. The computer readable medium of claim 21, further comprising using a computer data based search engine to obtain additional information regarding said relevant valid SNPs.

39. The computer readable medium of claim 38, wherein said additional information is selected from one or more of the group consisting of a compound, gene, cell, virus, sequence, and substance affecting said relevant valid SNP.

40. The computer readable medium of claim 21, wherein said instructions for annotating comprise assigning said relevant valid SNP to a gene location.

41. The computer readable medium of claim 21, wherein said instructions for annotating comprise assigning a gene name to said relevant valid SNPs.

42. A computer-implemented method for annotating SNPs onto candidate nucleic acid sequences comprising the steps of:
Receiving the candidate nucleic acid sequences;
generating subsequences of nucleic acid from said candidate nucleic acid sequences;
comparing, by one or more processors, each of said subsequences against one or more SNP databases using a sequence comparison algorithm to obtain relevant SNP output files;
analyzing said relevant SNP output files for relevant valid SNPs;
discarding said relevant valid SNPs located within repeat regions of said candidate nucleic acid sequence to remove intragenic SNPs annotated in the SNP databases that are not relevant for genotyping;
annotating said relevant valid SNPs onto the candidate nucleic acid sequences to assess the genetic content and redundancy of the relevant valid SNPs; and
outputting said annotated relevant valid SNPs to a display, a memory or another computer on a network, wherein said outputted annotated relevant valid SNPs are SNPs associated with a population susceptible to a disease or a condition.

43. The computer-implemented method of claim 42, further comprising recalculating nucleic acid positions for said relevant valid SNPs in said candidate nucleic acid sequence.

44. The computer-implemented method of claim 43, wherein said nucleic acid position is one or more selected from the group consisting of 5'UTR, promoter region, nucleic acid coding region, 3'UTR, and introns.

45. The computer-implemented method of claim 42, wherein said discarding comprises comparing relevant valid SNPs against the REPBASE database.

46. The computer-implemented method of claim 45, wherein said comparing is performed using an expectation value limit of about $10^{-3}$.

47. The computer-implemented method of claim 42, wherein said candidate nucleic acid sequence is gDNA.

48. The computer-implemented method of claim 42, wherein said candidate nucleic acid sequence is cDNA.

49. The computer-implemented method of claim 42, wherein said nucleic acid subsequences comprise a length between about 1000 bp and about 5000 bp.

50. The computer-implemented method of claim 49, wherein said nucleic acid subsequences have an overlap of nucleic acid sequence between flanking sequences within the range of about 100 bp to about 500 bp.

51. The computer-implemented method of claim 49, wherein said nucleic acid subsequences comprise a length of 1500 bp.

52. The computer-implemented method of claim 51, wherein said nucleic acid subsequences have an overlap of 250 by between flanking regions.

53. The computer-implemented method of claim 42, wherein said sequence comparison algorithm is BLAST.

54. The computer-implemented method of claim 53, wherein said comparing generates BLAST output files.

55. The computer-implemented method of claim 42, wherein said analyzing step comprises validating said relevant SNP output files.

56. The computer-implemented method of claim 55, wherein said validating comprises applying the following criteria:
SNP location within boundaries of hit length;
expectation value at least about $10^{-12}$ or below;
minimum identity is about 98% or above between SNP hit and query sequence; and
hit length is at least about 250 by or higher.

57. The computer-implemented method of claim 55, wherein said validating comprises applying the following criteria:
SNP location within boundaries of hit length;
expectation value at least about $10^{-12}$ or below;
minimum identity is about 98% or above between SNP hit and query sequence; and
hit length equals at least about 98% of the length of SNP entry in said one or more SNP databases.

58. The computer-implemented method of claim 42, further comprising using a computer data based search engine to obtain additional information regarding said relevant valid SNPs.

59. The computer-implemented method of claim 58, wherein said additional information is selected from one or more of the group consisting of a compound, gene, cell, virus, sequence, and substance affecting said relevant valid SNP.

60. The computer-implemented method of claim 42, wherein said annotating comprises assigning said relevant valid SNP to a gene location.

61. The computer-implemented method of claim 42, wherein said annotating comprises assigning a gene name to said relevant valid SNPs.

* * * * *

SEQUENCE LISTING

<160> NUMBER OF SEQ ID NOS: 15

<210> SEQ ID NO 1
<211> LENGTH: 1500
<212> TYPE: DNA
<213> ORGANISM: Homo sapiens

<400> SEQUENCE: 1

| gaaaactgta | tgacagaccc | aaacatcaac | ggggtgctta | gattctttga | tctcgggtca | 60 |
| gttccacaca | agacaggctc | tgtgttagtg | aggacccagt | ggtgttttg | aacaggcggc | 120 |
| aggataacaa | tggtatataa | aataaatgca | gagaaagacc | tccacatcaa | gccaacccct | 180 |
| cctccctacc | tgtaagtttt | ccacctgagt | gagctctggc | tccagctgca | cttgtcaaac | 240 |
| tcccattgtt | agagcacaga | taaatgcttc | cggccaccca | agcaggagag | gcccacctca | 300 |
| acttaagggc | tactctattt | tagttttccg | tagctggaga | ttgagtatca | cgcttttcta | 360 |
| atcttgtgct | tctgaaaggg | ccctgttctc | tcttgaaccc | cacccctcc | tcctttcaca | 420 |
| gatcaaatac | caagtacatt | ggacagatag | aagttcgaat | gagaaaatgc | attttaataa | 480 |
| aatcccattg | attttttgtgg | atgtaagtca | aggaacaggc | acctaaagag | tcttccatcc | 540 |
| cctgccgtct | cccgcctctc | tcctgaccta | caccgggcgg | tcatacatcg | attggcttcc | 600 |
| tagataatag | atcgtgccac | ccggtaggga | cctctgggga | cgcgccggga | gctggaagag | 660 |
| tcgcacgcag | cagcccaacc | ctgagttaat | caaactagca | acaggatctc | aagcagcagc | 720 |
| gacggcggtg | gcaagagtag | cggtgacggc | ggcggcggcg | gcggcggcag | cattatgcgt | 780 |
| gattactgac | aggcaccagc | tgctgccgcc | acagccgtct | caaacgcact | atgtggactc | 840 |

```
tccgatctag aggcagattc ctgactaatc ccagagggct ggcccagcct gtgctccccg      900
ggctgctagg aagcgatgac cactcttgtt agcccaagtt gaagaaagcc gggctgtgcc      960
tgggagccga gagaggcggt aatatttaga agctgcacag gagaggaaca tgaactgacg     1020
agtaaacatg tatggaaatt attctcactt catgaagttt cccgcaggct atggaggtaa     1080
gtatctccct tgggcttcac tgcgtggacc tgtatgagag actgagaaga aattgggaaa     1140
tacgaatgac tggattagta ttgaattaaa aggagaacat atatgtttat atgcatatat     1200
agtgtgtata tagcgtttca gcgtgtgtgt gcacgcgtgc atgagagagg agaggaggaa     1260
agaatggtct gtaggtgagg atacgtttgc atatcagaat gaggatacgg ggatattcta     1320
aggagagagt aaaccaacat gcttgagaat gtgtctgaga caaagataga ataagagcat     1380
tgttataacc cagtgtgttt gtgcgggtgt gaaaagtgga agagttaacg gggaattact     1440
atgatgttcc tattagccaa cttgtaatga gaaaaaatgt gattaaaaag gttttgccta     1500

<210> SEQ ID NO 2
<211> LENGTH: 1500
<212> TYPE: DNA
<213> ORGANISM: Homo sapiens

<400> SEQUENCE: 2
agaggaggaa agaatggtct gtaggtgagg atacgtttgc atatcagaat gaggatacgg       60
ggatattcta aggagagagt aaaccaacat gcttgagaat gtgtctgaga caaagataga      120
ataagagcat tgttataacc cagtgtgttt gtgcgggtgt gaaaagtgga agagttaacg      180
gggaattact atgatgttcc tattagccaa cttgtaatga gaaaaaatgt gattaaaaag      240
gttttgccta tcttgagggt tcctgggata cttttgtaaca agggcatgat tgttttactc      300
aaaagcagat ttccctttaa ttggattttt aaaagaaaa catagtgctt taatttgcta      360
ctgtgttttc cttcccctgt tttctttcct ttgatttgct aatagcctct tctctcctcc      420
cctgctgctg cccccaattc tactgcaaga gttgctgcaa tcacttccac tctggggta      480 gagatctggg gatgggggt tgggctctt agagaattgg caaactgaag attcaagtca      540
ccgtgccagg cagggcagcc cagtcacact tcacagaagc ttccggagac taggtcctca      600
ggctgcctta acgcccaagc acatctgtcc caaggatccc ttgatttagt gacagaaaca      660
gtacagccgc ccagctctga gtaaatggaa gcaacagctg accaactggc ctgtcgcttg      720
tcagttggag gcatgcagct tatgttgctg ggagccaaag aaagattctg gcaggcaaga      780
cagcagaaat tcttataagg ttttgaaaat tgaaaagtcc ctgctctcca gacttcctcc      840
gtggaccaat tcatctgaag gcttgggact aaagcttgcc taacttggct gggcagaacc      900
ccctgggagg catggtgaca cactgcaagg tagaagtgat ctctgtcacc aggaggtgtt      960
agacctggga gtttgcacat tcattccaggg tagtttttat gaggcaggca tggtgttggg     1020
cactgggaat acaaatatga atgagacaca gtctctgccc tttgggactg gggcaggctt     1080
gttacacagg cacattataa tactgcatga tgtgtgtaat agcaaacgta ggttgtactt     1140
ggacttgggg tgagggccat ggaaatgttc ccgaggtgat gttcaagttc tttgggccag     1200
tctgatgaca gagtgagagc ggtggccaat gctgtgacct gggcatttga tctctagtct     1260
atggttgggc tccagatgtg aaaagcctcc tcaattccca cctcagtccc attcagagct     1320
gagaattgct ttttcctta catcttagtt catttgtaag aggtgcatgc tcattttcag     1380
ccagattcgt gggcccccca aggtctgtga gactgtggcc tcattaatgc caaagagacc     1440
cttggagaca gttggggtga ataaaagggt tgaagctaga aggatttagg gagagaacta     1500
```

-continued

<210> SEQ ID NO 3
<211> LENGTH: 18
<212> TYPE: DNA
<213> ORGANISM: Homo sapiens

<400> SEQUENCE: 3
tctctagtct atggttgg                                              18

<210> SEQ ID NO 4
<211> LENGTH: 178
<212> TYPE: DNA
<213> ORGANISM: Homo sapiens

<400> SEQUENCE: 4
gaattcctca ttcctggaca gtccggaggc agacctgcca ctttgttttg agcaaactgt     60
tctggtgtgg attcccttgg gctacctatg gctcctggcc ccctggcagc ttctccacgt   120
gtataaatcc aggaccaaga gatcctctac caccaaactc tatcttgcta agcaggta     178

<210> SEQ ID NO 5
<211> LENGTH: 178
<212> TYPE: DNA
<213> ORGANISM: Homo sapiens

<400> SEQUENCE: 5
gaattcctca ttcctggaca gtccggaggc agacctgcca ctttgttttg agcaaactgt     60
tctggtgtgg attcccttgg gctwcctatg gctcctggcc ccctggcagc ttctccacgt   120
gtataaatcc aggaccaaga gatcctctac caccaaactc tatcttgcta agcaggta     178

<210> SEQ ID NO 6
<211> LENGTH: 62
<212> TYPE: DNA
<213> ORGANISM: Homo sapiens

<400> SEQUENCE: 6
gtcttcgttc cagacgcagt ccaggaatca tgctggagaa gttctgcaac tctactttt      60 gg                                                                   62

<210> SEQ ID NO 7
<211> LENGTH: 62
<212> TYPE: DNA
<213> ORGANISM: Homo sapiens

<400> SEQUENCE: 7
gtcttygttc cagacgcagt ccaggaatca tgctggagaa gttctgcaac tctactttt      60 gg                                                                   62

<210> SEQ ID NO 8
<211> LENGTH: 61
<212> TYPE: DNA
<213> ORGANISM: Homo sapiens

<400> SEQUENCE: 8
caggacccca tcctgttctc tggaagcctg aggatgaatc tcgacccttt caacaactac     60
t                                                                    61

<210> SEQ ID NO 9
<211> LENGTH: 61
<212> TYPE: DNA
<213> ORGANISM: Homo sapiens

```
<400> SEQUENCE: 9
caggacccca tcctgttctt tggaaacctg aggatgaatc ttgaccctt caacaactac    60
t                                                                  61

<210> SEQ ID NO 10
<211> LENGTH: 58
<212> TYPE: DNA
<213> ORGANISM: Homo sapiens

<400> SEQUENCE: 10
gaattcctca ttcctggaca gtccggaggc agacctgcca ctttgttttg agcaaact    58

<210> SEQ ID NO 11
<211> LENGTH: 46
<212> TYPE: DNA
<213> ORGANISM: Homo sapiens

<400> SEQUENCE: 11
gaccaagaga tcctctacca ccaaactcta tcttgctaag caggta                 46

<210> SEQ ID NO 12
<211> LENGTH: 58
<212> TYPE: DNA
<213> ORGANISM: Homo sapiens

<400> SEQUENCE: 12
gaattcctca ttcctggaca gtccggaggc agacctgcca ctttgttttg agcaaact    58

<210> SEQ ID NO 13
<211> LENGTH: 46
<212> TYPE: DNA
<213> ORGANISM: Homo sapiens

<400> SEQUENCE: 13
gaccaagaga tcctctacca ccaaactcta tcttgctaag caggta                 46

<210> SEQ ID NO 14
<211> LENGTH: 23
<212> TYPE: DNA
<213> ORGANISM: Homo sapiens

<400> SEQUENCE: 14
acgactgacg aatgacactg act                                          23

<210> SEQ ID NO 15
<211> LENGTH: 23
<212> TYPE: DNA
<213> ORGANISM: Homo sapiens

<400> SEQUENCE: 15
actgctgact gactgctgtg act                                          23
```